United States Patent [19]
Takayama et al.

[11] Patent Number: 5,817,670
[45] Date of Patent: Oct. 6, 1998

[54] NAPHTHYRIDINE DERIVATIVES AND PHARMACEUTICAL COMPOSITIONS THEREOF

[75] Inventors: Kazuhisa Takayama; Masahiro Iwata; Yoshinori Okamoto; Motonori Aoki, all of Ibaraki; Akira Niwa, Chiba; Yasuo Isomura, Ibaraki, all of Japan

[73] Assignee: Yamanouchi Pharmaceutical Co., Ltd., Tokyo, Japan

[21] Appl. No.: 776,295

[22] PCT Filed: Aug. 28, 1995

[86] PCT No.: PCT/JP95/01700

§ 371 Date: Jan. 30, 1997

§ 102(e) Date: Jan. 30, 1997

[87] PCT Pub. No.: WO96/06843

PCT Pub. Date: Mar. 7, 1996

[30] Foreign Application Priority Data

Aug. 29, 1994 [JP] Japan .................................. 6-203677
Feb. 7, 1995 [JP] Japan .................................. 7-019113

[51] Int. Cl.⁶ ...................... A61K 31/435; C07D 471/04
[52] U.S. Cl. ........................ 514/300; 546/122; 546/123
[58] Field of Search ................................ 546/122, 123; 514/300

[56] References Cited

U.S. PATENT DOCUMENTS 4,775,686  10/1988  Blythin et al. .......................... 514/300

FOREIGN PATENT DOCUMENTS 55-164682  6/1979  Japan .

OTHER PUBLICATIONS

El–Taweel, J. Prakt. Chem. 332(5), pp. 762–766; Chemical Abstracts vol. 114, 185431 (1991).

Primary Examiner—Bernard Dentz
Attorney, Agent, or Firm—Burgess, Ryan & Wayne

[57] ABSTRACT

1,8-Naphthyridine derivatives represented by the following general formula (I), salts thereof, hydrates thereof and solvates thereof.

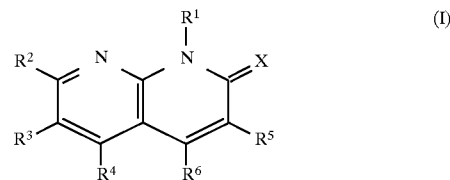

They have an activity to inhibit type IV phosphodiesterase and are useful as agents for the prevention and treatment of respiratory diseases, inflammatory diseases accompanying organ transplantation, systemic or local arthropathy, proliferative diseases, micturition-related diseases and diseases in which tumor necrosis factor (TNF) and other cytokine (IL-1, IL-6 or the like) are concerned.

20 Claims, No Drawings

NAPHTHYRIDINE DERIVATIVES AND PHARMACEUTICAL COMPOSITIONS THEREOF

This application is a 371 of PCT/JP95/01700 filed Aug. 28, 1998 published as WO96/06843 Mar. 7, 1996.

TECHNICAL FIELD

The present invention relates to 1,8-naphthyridine derivatives and salts thereof. These substances are useful in prevention or treatment of diseases in which type IV phosphodiesterase is concerned, particularly bronchial asthma and the like.

BACKGROUND ART

Asthma is a respiratory disease which repeats stridor and attack due to airway contraction. The number of the asthma patients has been increasing constantly and is considered to further increase in the future.

Main morbid states of asthma are a) sudden contraction of smooth muscle which surrounds the airway and b) inflammatory reaction caused by the activation of infiltrative cells in respiratory organs including the lungs. Therefore, it is considered that inhibition of the airway smooth muscle contraction and suppression or prevention of the activation of infiltrative cells are effective means for the treatment of symptoms of asthma.

For the treatment of asthma, compounds having a xanthine nucleus such as aminophylline and theophylline are used. These compounds are used as bronchial dilating agents since they suppress contraction of airway smooth muscle through the increment of the concentration of cyclic adenosine 3', 5'-monophosphate (cAMP) in the cells of the airway smooth muscle, which is effected by the inhibition of phosphodiesterase (PDE) as a cAMP-hydrolyzing enzyme [*Thorax*, 46, 512–523 (1991)].

However, compounds having a xanthine nucleus generate systemic side effects such as decrease in blood pressure, cardiotonic action and the like [*J. Cyclic Nucleotide and Protein Phosphorylation Res.*, 10, 551–564 (1985)] and, therefore, it is necessary to monitor its concentration in blood in order to prevent these systemic side effects, resulting in the complicated use. In addition, xanthine derivatives do not exert clear effect against asthma when it involves infiltration of inflammatory cells. From these reasons, these compound are not satisfactory as a therapeutic agent.

In addition, β-stimulators such as procaterol and formoterol have been used as a bronchial dilating agent (*Eur. Respir. J.*, 5, 1126–1136 (1992)), but they are known to generate side effects such as finger tremor, palpitation and the like, when the dose is increased because of their aptness to generate desensitization.

Studies conducted thereafter have revealed that the PDE, an enzyme which hydrolyses cAMP, is divided into at least four different types of I to IV having different distributions and functions [*Pharmacological Therapy*, 51, 13–33 (1991)]. Particularly, the type IV PDE hydrolyses cAMP in a specific fashion without acting upon cyclic guanosine 3', 5'-monophosphate (cGMP) among nucleotides, and its presence is found in both airway smooth muscle and infiltrative cells.

Concentration of cAMP in cells is set by the balance of the cAMP production rate by adenylate cyclase and the cAMP degradation rate by PDE. In consequence, intracellular cAMP concentration can be increased by stimulating adenylate cyclase or inhibiting PDE. Increase in the intracellular cAMP concentration induces suppression of contraction of the airway smooth muscle and suppression of the activation of inflammatory cells [*Clin. Exp. Allergy*, 22, 337–344 (1992), *Drugs of the Future*, 17, 799–807 (1992)].

On the other hand, naphthyridine derivatives are disclosed, for example, in an unexamined published Japanese patent application (Kokai) No. 55-164682 and International Patent Publication 94/12499 (1994).

Of these references, an unexamined published Japanese patent application (Kokai) No. 55-164682 discloses 2-oxo-4-phenyl-1,5,7-trimethyl-2H-1,8-naphthyridine which shows diuretic action, but does not disclose the antiasthmatic action by the selective suppression of type IV phosphodiesterase.

Also, International Patent Publication 94/12499 (1994) discloses a compound having the following general formula which has an activity to inhibit phosphodiesterase.

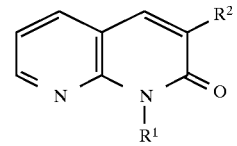

(See the aforementioned reference for $R^1$ and $R^2$ in the above formula).

However, in comparison with these compounds, the compound of the present invention represented by the general formula which will be described later has a structural difference in which it has a substituent having a ring structure at the 4-position of the naphthyridine nucleus and is more markedly different in terms of its excellent action to inhibit type IV phosphodiesterase.

The compound of the present invention is expected to be an antiasthmatic agent because of its selective action to inhibit type IV phosphodiesterase. That is, because of its action to inhibit contraction of the airway smooth muscle and activation of infiltrative cells, it exerts characteristic effects to inhibit not only the airway contraction which causes difficult breathing but also the inflammatory reactions considered to be the origin of chronic asthmatic symptoms, and it hardly generates systemic actions which are common in asthma treating drugs such as aminophylline (*J. P. E. T.*, 257, 741–747 (1991)), so that the compound of the present invention is expected to be an antiasthmatic drug having high safety and efficacy.

DISCLOSURE OF THE INVENTION

The inventors of the present invention have conducted extensive studies on compounds which show inhibitory activity against type IV phosphodiesterase and accomplished the present invention by creating novel naphthyridine derivatives having the following general formula (I) and finding that they have excellent type IV phosphodiesterase inhibiting activity.

Accordingly, the present invention relates to 1,8-naphthyridine derivatives represented by the following general formula (I), salts thereof, hydrates thereof and solvates thereof.

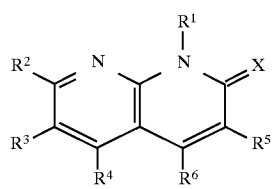

(Each symbol in the formula represents the following meaning;

X: an oxygen atom or a sulfur atom, $R^1$: a lower alkyl group which may be substituted with a group described in the A group, a lower alkenyl group, a lower alkynyl group, a cycloalkyl group, a cycloalkyl-lower alkyl group, an aryl group which may be substituted with a group described in the B group, an aralkyl group which may be substituted with a group described in the B group, a five- or six-membered monocyclic heteroaryl group, or a five- or six-membered monocyclic heteroaryl-lower alkyl group, $R^2$, $R^3$ and $R^4$: may be the same or different from one another and each represents a hydrogen atom, a halogen atom, a lower alkyl group, a hydroxyl group, a lower alkoxy group, a lower alkylcarbonyl group, a trihalogenomethyl group, a nitro group, a cyano group, an amino group, a mono- or di-lower alkylamino group, a carboxyl group, a lower alkoxycarbonyl group, a carbamoyl group, a mono- or di-lower alkylcarbamoyl group, a lower alkylcarbonylamino group, an aryl group, or a cycloalkyl group, $R^5$: a hydrogen atom or a lower alkyl group, $R^6$: an aryl group which may be substituted with a group described in the C group, a five- or six-membered monocyclic heteroaryl group which may be substituted with a group described in the C group, a cycloalkyl group, or an adamantyl group, A group: a halogen atom, a hydroxyl group, a lower alkoxy group, a cyano group, a nitro group, an amino group, a mono- or di-lower alkylamino group, a carboxyl group, a lower alkoxycarbonyl group, a lower alkylcarbonyl group, a carbamoyl group or a mono- or di-lower alkylcarbamoyl group, B group: a lower alkyl group or a group described in the A group, C group: a halogen atom, a hydroxyl group, a lower alkoxy group, a lower alkylcarbonyl group, a nitro group, a cyano group, an amino group, a mono- or di-lower alkylamino group, a carboxyl group, a lower alkoxycarbonyl group, a carbamoyl group, a mono- or di-lower alkylcarbamoyl group or a lower alkylcarbonylamino group, or a lower alkyl group which may be substituted with these groups, (with the proviso that, when each of $R^1$, $R^2$ and $R^4$ is a methyl group and each of $R^3$ and $R^5$ is a hydrogen atom, $R^6$ represents an aryl group which is substituted with a group described in the C group, a five- or six-membered monocyclic heteroaryl group which may be substituted with a group described in the C group, a cycloalkyl group or an adamantyl group).)

Among the compounds of the present invention, a preferred compound is a 1,8-naphthyridine derivative or a salt thereof in which, in the general formula (I), $R^1$ is a lower alkyl group which may be substituted with a group described in the A group, a lower alkenyl group, a lower alkynyl group, a cycloalkyl group, a cycloalkyl-lower alkyl group, a phenyl group, a phenyl-lower alkyl group, a pyridyl group or a pyridyl-lower alkyl group, $R^2$, $R^3$ and $R^4$ may be the same or different from one another and each represents a hydrogen atom, a halogen atom, a lower alkyl group, a hydroxyl group, a lower alkoxy group, a lower alkylcarbonyl group, a trihalogenomethyl group, a phenyl group or a cycloalkyl group, $R^6$ is a phenyl group which may be substituted with a group described in the C group, a thienyl group, a thiazolyl group, a cycloalkyl group or an adamantyl group, and C group is a halogen atom, a hydroxyl group, a lower alkoxy group, a lower alkylcarbonyl group, a nitro group, a cyano group, an amino group, a mono- or di-lower alkylamino group, a carboxyl group, a lower alkoxycarbonyl group, a carbamoyl group, a mono- or di-lower alkylcarbamoyl group or a lower alkylcarbonylamino group, or a lower alkyl group which may be substituted with a halogen atom or hydroxyl group.

More preferred is a 1,8-naphthyridine derivative or a salt thereof in which $R^1$ is a lower alkyl group which may be substituted with a group selected from a cyano group, a mono- or di-lower alkylamino group, a carboxyl group, a lower alkoxycarbonyl group, a lower alkylcarbonyl group or a carbamoyl group, a lower alkenyl group, a lower alkynyl group, a cycloalkyl group, a cycloalkyl-lower alkyl group, a phenyl group, a phenyl-lower alkyl group, a pyridyl group or a pyridyl-lower alkyl group, $R^6$ is a phenyl group which may be substituted with a group selected from a halogen atom, a hydroxyl group, a lower alkyl group, a lower alkoxy group, a nitro group, a cyano group, an amino group or a trifluoromethyl group, thienyl group, thiazolyl group, a cycloalkyl group or an adamantyl group, and $R^2$, $R^3$ and $R^4$ may be the same or different from one another and each represents a hydrogen atom, a lower alkyl group, a trifluoromethyl group or a phenyl group, and particularly preferred is a 1,8-naphthyridine derivative or a salt thereof in which $R^6$ is a phenyl group which may be substituted with a halogen atom, a hydroxyl group, a lower alkyl group, a lower alkoxy group, a nitro group, a cyano group or an amino group, a 1,8-naphthyridine derivative or a salt thereof in which $R^6$ is a cycloalkyl group or an adamantyl group, a 1,8-naphthyridine derivative or a salt thereof in which $R^5$ is a hydrogen atom, or a 1,8-naphthyridine derivative or a salt thereof in which X is an oxygen atom.

The present invention also relates to a type IV phosphodiesterase inhibitor which comprises, as its active ingredient, a 1,8-naphthyridine derivative represented by the following general formula (I), a salt thereof, a hydrate thereof or a solvate thereof.

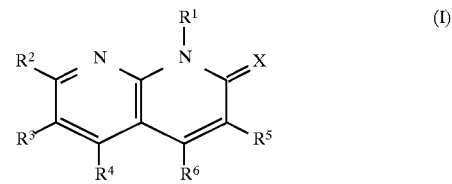

(Each symbol in the formula represents the following meaning;

X: an oxygen atom or a sulfur atom, $R^1$: a lower alkyl group which may be substituted with a group described in the A group, a lower alkenyl group, a lower alkynyl group, a cycloalkyl group, a cycloalkyl-lower alkyl group, an aryl group which may be substituted with a group described in the B group, an aralkyl group which may be substituted with a group described in the B group, a five- or six-membered monocyclic heteroaryl group, or a five- or six-membered monocyclic heteroaryl-lower alkyl group, $R^2$, $R^3$ and $R^4$: may be the same or different from one another and each represents a hydrogen atom, a halogen atom, a lower alkyl group, a hydroxyl group, a lower alkoxy group, a lower alkylcarbonyl group, a trihalogenomethyl group, a nitro group, a cyano group, an amino group, a mono- or di-lower alkylamino group, a carboxyl group, a lower alkoxycarbonyl group, a carbamoyl group, a mono- or di-lower alkylcarbamoyl group, a lower alkylcarbonylamino group, an aryl group, or a cycloalkyl group, $R^5$: a hydrogen atom or a lower alkyl group, $R^6$: an aryl group which may be substituted with a group described in the C group, a five- or six-membered monocyclic heteroaryl group which may be substituted with a group described in the C group, a cycloalkyl group, or an adamantyl group, A group: a halogen atom, a hydroxyl group, a lower alkoxy group, a cyano group, a nitro group, an amino group, a mono- or di-lower alkylamino group, a carboxyl group, a lower alkoxycarbonyl group, a lower alkylcarbonyl group, a carbamoyl group or a mono- or di-lower alkylcarbamoyl group, B group: a lower alkyl group or a group described in the A group, C group: a halogen atom, a hydroxyl group, a lower alkoxy group, a lower alkylcarbonyl group, a nitro group, a cyano group, an amino group, a mono- or di-lower alkylamino group, a carboxyl group, a lower alkoxycarbonyl group, a carbamoyl group, a mono- or di-lower alkylcarbamoyl group or a lower alkylcarbonylamino group, or a lower alkyl group which may be substituted with these groups.)

Illustratively, the type IV phosphodiesterase inhibitor of the present invention is useful as an agent for prevention or treatment of respiratory diseases (for example, bronchial asthma (including atopic asthma), chronic bronchitis, pneumonia, adult respiratory distress syndrome (ARDS) and the like), inflammatory diseases (for example, atopic dermatitis, conjunctivitis, urticaria, acquired immunodeficiency syndrome (AIDS), keloid formation, rhinitis, iridocyclitis, gingivitis, periodontitis, alveolar pyorrhea, gastritis, ulcerative colitis, Crohn disease, gastrointestinal ulcer, esophagitis, myositis, encephalitis (myasthenia gravis, multiple sclerosis and neuritis), hepatitis, cicatrization, nephritis (including proliferative nephritis), peritonitis, pleurisy, scleritis, scleroderma, burn injury and the like), systemic or local arthropathy (for example, osteoarthrosis of knee, gouty arthritis, chronic rheumatoid arthritis, malignant rheumatoid, psoriatic arthritis and the like), inflammation due to organ transplantation and the like (for example, reperfusion injury, graft versus host reaction and the like), diseases related to micturition (for example, diabetes insipidus, urethritis, urinary incontinence, cystitis, irritable bladder, neurogenic bladder, uremia, tubular disorder, pollakiuria, urinary retention and the like), diseases in which tumor necrosis factor (TNF) and other cytokine (IL-1, IL-6 and the like) are concerned (for example, psoriasis, rheumatoid arthritis, ulcerative colitis, Crohn disease, sepsis, septic shock, endotoxin shock, Gram negative bacillus sepsis, toxic shock syndrome, nephritis, hepatitis, infection (bacterial and viral), circulatory failure (heart failure, arteriosclerosis, myocardial infarction, stroke) and the like.

Particularly, it is useful as a drug for the prevention or treatment of respiratory diseases (for example, bronchial asthma (including atopic asthma), chronic bronchitis, pneumonia, adult respiratory distress syndrome (ARDS) and the like), inflammatory diseases (for example, atopic dermatitis, conjunctivitis, urticaria, acquired immunodeficiency syndrome (AIDS), keloid formation, rhinitis, iridocyclitis, gingivitis, periodontitis, alveolar pyorrhea, gastritis, ulcerative colitis, Crohn disease, gastrointestinal ulcer, esophagitis, myositis, encephalitis (myasthenia gravis, multiple sclerosis and neuritis), hepatitis, cicatrization, nephritis (including proliferative nephritis), peritonitis, pleurisy, scleritis, scleroderma, burn injury and the like), and diseases in which tumor necrosis factor (TNF) and other cytokine (IL-1, IL-6 and the like) are concerned (for example, psoriasis, rheumatoid arthritis, ulcerative colitis, Crohn disease, sepsis, septic shock, endotoxin shock, Gram negative bacillus sepsis, toxic shock syndrome, nephritis, hepatitis, infection (bacterial and viral), circulatory failure (heart failure, arteriosclerosis, myocardial infarction, stroke) and the like).

Most particularly, it is useful as a drug for the prevention or treatment of respiratory diseases (for example, bronchial asthma (including atopic asthma), chronic bronchitis, pneumonia, adult respiratory distress syndrome (ARDS) and the like), especially, as a preventing or treating agent for bronchial asthma.

The following describes the compound of the present invention further in detail.

Unless otherwise indicated, the term "lower" as used in the definition of the general formula of the present specification means a straight or branched carbon chain having 1 to 6 carbon atoms.

Illustrative examples of the "lower alkyl group" include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and the like. Of these groups, alkyl groups having 1 to 4 carbon atoms such as methyl, ethyl, propyl, isopropyl, butyl and the like are preferred, and methyl, ethyl and propyl groups are more preferred and methyl and ethyl groups are particularly preferred.

Illustrative examples of the "lower alkenyl group" include straight or branched alkenyl groups having 2 to 6 carbon atoms, such as vinyl, propenyl, butenyl, methylpropenyl, ethylpropenyl, dimethylvinyl, pentenyl, methylbutenyl, dimethylpropenyl, ethylpropenyl, hexenyl, dimethylbutenyl, methylpentenyl and the like. Propenyl and butenyl groups are preferred, and a propenyl group is more preferred.

Illustrative examples of the "lower alkynyl group" include straight or branched alkynyl groups having 2 to 6 carbon atoms, such as ethynyl, propynyl, butynyl, methylpropynyl, pentynyl, methylbutynyl, hexynyl and the like. Ethynyl and propynyl groups are preferred and an ethynyl group is particularly preferred.

Illustrative examples of "cycloalkyl group" include those having 3 to 8 carbon atoms, such as cyclopropyl, cyclobutyl, cyclopentyl, cyclohexyl, cycloheptyl, cyclooctyl and the like. As the cycloalkyl group of $R^6$, cyclopropyl, cyclobutyl, cyclopentyl, cyclohexyl and cycloheptyl groups are preferred, of which cyclopentyl, cyclohexyl and cycloheptyl groups are more preferred and a cyclohexyl group is particularly preferred. Also, as the cycloalkyl group of $R^1$, cyclopropyl, cyclobutyl, cyclopentyl and cyclohexyl groups are preferred, of which cyclopropyl and cyclobutyl groups are more preferred and a cyclopropyl group is particularly preferred.

The term "cycloalkyl-lower alkyl group" as used herein means a group in which an any hydrogen of the aforementioned lower alkyl group is substituted with a cycloalkyl group, and its illustrative examples include cyclopropylmethyl, cyclopropylethyl, cyclopropylpropyl, cyclobutylmethyl and the like, of which cyclopropylmethyl is preferred.

The term "aryl group" means an aromatic hydrocarbon group preferably those having 6 to 14 carbon atoms. The illustrative examples include phenyl, tolyl, xylyl, biphenyl, naphthyl, indenyl, anthryl and phenanthryl groups, more preferably phenyl or naphthyl group, most preferably a phenyl group.

The term "aralkyl group" as used herein means a group in which an any hydrogen of the aforementioned "lower alkyl group" is substituted with an aryl group. The illustrative examples include phenylalkyl groups such as benzyl, phenetyl, phenylpropyl, phenylbutyl and the like and naphthylalkyl groups such as naphthylmethyl, naphthylethyl and the like.

The term "five- or six-membered monocyclic heteroaryl group" as used herein means a five- or six-membered monocyclic heteroaryl group having 1 to 4 hetero atoms comprised of an oxygen atom, a sulfur atom and a nitrogen atom. The illustrative examples include furyl, thienyl, pyrrolyl, imidazolyl, thiazolyl, pyrazolyl, isothiazolyl, isoxazolyl, pyridyl, pyrimidinyl, pyridazinyl, pyrazinyl, triazolyl, tetrazolyl and the like. Of these groups, preferred five- or six-membered monocyclic heteroaryl groups as defined in $R^6$ are furyl, thienyl, pyrrolyl, imidazolyl, thiazolyl, isothiazolyl, pyridyl, pyrimidinyl, pyrazinyl and the like, and most preferably thienyl and thiazolyl.

Also, preferred five- or six-membered monocyclic heteroaryl groups as defined in $R^1$ are thienyl, pyrrolyl, imidazolyl, thiazolyl, isothiazolyl, pyridyl, pyrimidinyl, pyrazinyl and the like, most preferably pyridyl.

The "halogen atom" means a fluorine atom, a chlorine atom, a bromine atom or an iodine atom, and illustrative examples of "trihalogenomethyl group" include trifluoromethyl, trichloromethyl, tribromomethyl, triiodomethyl, dichlorobromomethyl and the like.

Examples of the "lower alkoxy group" include methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy, hexyloxy and the like, of which methoxy is preferred.

Examples of the "lower alkylcarbonyl group" include formyl, acetyl, propionyl, butylyl, valeryl, pivaloyl and the like.

The term "mono- or di-lower alkylamino group" as used herein means an amino group in which one or two hydrogen atoms in the amino group are substituted with the aforementioned lower alkyl group, and its illustrative examples include methylamino, ethylamino, propylamino, dimethylamino, diethylamino, dipropylamino and the like. Of these groups, methylamino and dimethylamino are preferred.

Examples of the "lower alkoxycarbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxy (amyloxy)carbonyl, isopentyloxycarbonyl, tert-pentyloxycarbonyl, neopentyloxycarbonyl, 2-methylbutoxycarbonyl, 1,2-dimethylpropoxycarbonyl, 1-ethylpropoxycarbonyl, hexyloxycarbonyl and the like. Of these groups, methoxycarbonyl and ethoxycarbonyl are preferred.

The term "mono- or di-lower alkylcarbamoyl group" as used herein means a carbamoyl group in which one or two hydrogen atoms of the carbamoyl group are substituted with the aforementioned lower alkyl group, and its illustrative examples include methylcarbamoyl, ethylcarbamoyl, propylcarbamoyl, dimethylcarbamoyl and the like.

The term "lower alkylcarbonylamino group" as used herein means an amino group in which one hydrogen atom in the amino group are substituted with the aforementioned lower alkylcarbonyl group. That is, it means a "lower alkylamido" which includes methylamido, ethylamido, propylamido and the like.

The term "lower alkyl group which may be substituted with a group described in the A group" as used herein means the aforementioned "lower alkyl group" and other groups in which any hydrogen atom in the aforementioned "lower alkyl group" is substituted with an any group described in the A group.

Also, the term "aryl group which may be substituted with a group described in the B group" or "aryl group which may be substituted with a group described in the C group" as used herein means the aforementioned "aryl group" and groups in which any hydrogen atom in the aforementioned "aryl group" are substituted with any 1 to 4 groups described in the B group or with any 1 to 4 groups described in the C group.

The term "aralkyl group which may be substituted with a group described in the B group" as used herein means the aforementioned "aralkyl group" and groups in which any hydrogen atom in the aryl moiety of the aforementioned "aralkyl group" are substituted with any 1 to 4 groups described in the B group.

Also, the term "five- or six-membered monocyclic heteroaryl-lower alkyl group" as used herein means a group in which any hydrogen atom in the aforementioned "lower alkyl group" is substituted with the aforementioned "five- or six- membered monocyclic heteroaryl group".

For example, chloromethyl, fluoromethyl, 2-chloroethyl, 2-fluoropropyl, 3-bromobutyl and a trihalogenomethyl (e.g., trifluoromethyl) can be exemplified as the "lower alkyl group substituted with halogen atom".

Illustrative examples of the "lower alkyl group substituted with mono- or di-lower alkylamino group" include methylaminomethyl, dimethylaminomethyl, ethylaminomethyl, diethylaminomethyl, ethylmethylaminomethyl, propylaminomethyl, butylaminomethyl, pentylaminomethyl, hexylaminomethyl, methylaminoethyl, ethylaminoethyl, propylaminoethyl, butylaminoethyl, pentylaminoethyl, hexylaminoethyl, methylaminopropyl, ethylaminopropyl, propylaminopropyl, butylaminopropyl, pentylaminopropyl, hexylaminopropyl, methylaminobutyl, ethylaminobutyl, propylaminobutyl, butylaminobutyl, pentylaminobutyl, hexylaminobutyl, methylaminopentyl, ethylaminopentyl, propylaminopentyl, butylaminopentyl, pentylaminopentyl, hexylaminopentyl, methylaminohexyl, ethylaminohexyl, propylaminohexyl, butylaminohexyl, pentylaminohexyl, hexylaminohexyl and the like, of which dimethylaminoethyl is preferred.

Illustrative examples of the "lower alkyl group substituted with lower alkoxycarbonyl group" include methoxycarbonylmethyl, ethoxycarbonylmethyl, propoxycarbonylmethyl, isopropoxycarbonylmethyl, butoxycarbonylmethyl, isobutoxycarbonylmethyl, sec-butoxycarbonylmethyl, tert-butoxycarbonylmethyl, pentyloxycarbonylmethyl, isopentyloxycarbonylmethyl, neopentyloxycarbonylmethyl, hexyloxycarbonylmethyl, methoxycarbonylethyl, methoxycarbonylpropyl, ethoxycarbonylethyl, ethoxycarbonylpropyl, propoxycarbonylpropyl and the like, of which ethoxycarbonylmethyl is preferred.

Examples of the "aryl group substituted with halogen atom" include 2-fluorophenyl, 2-chlorophenyl, 2-bromophenyl, 2-iodophenyl, 3-chlorophenyl, 3-bromophenyl, 4-chlorophenyl, 4-bromophenyl, 2-chlorotolyl, 2-bromotolyl, 2-chloroxylyl, 2-bromoxylyl, 2-chloronaphthyl, 2-bromonaphthyl, 2-chloroindenyl, 2-bromoindenyl, 2-chloroanthryl, 2-bromoanthryl, 2-chlorophenanthryl, 2-bromophenanthryl, 2,3-dichlorophenyl, 2,4-dichlorophenyl, 2,5-dichlorophenyl, 2,6-dichlorophenyl, 2,3,4-trichlorophenyl, 2,4,5-trichlorophenyl, 2,3,4,5-tetrachlorophenyl and the like, of which 3-chlorophenyl and 3-bromophenyl are preferred.

Examples of the "aryl group substituted with lower alkoxy group" include 2-methoxyphenyl, 3-methoxyphenyl, 4-methoxyphenyl, 2-ethoxyphenyl, 2-propoxyphenyl, 2-butoxyphenyl, 2-pentyloxy(2-amyloxy)phenyl, hexyloxyphenyl, 2-methoxytolyl, 2-methoxyxylyl, 2-methoxynaphthyl, 2-methoxyindenyl, 2-methoxyanthryl, 2-methoxyphenanthryl and the like, of which 2-methoxyphenyl and 3-methoxyphenyl are preferred.

The term "lower alkyl group which may be substituted with these groups" as described in the C group means a lower alkyl group which may be substituted with the other group described in the C group, namely a halogen atom, a hydroxyl group, a lower alkoxy group, a lower alkylcarbonyl group, a nitro group, a cyano group, an amino group, a mono- or di-lower alkylamino group, a carboxyl group, a lower alkoxycarbonyl group, a carbamoyl group, a mono- or di-lower alkylcarbamoyl group or a lower alkylcarbonylamino group.

Since the compound (I) of the present invention has one or a plurality of asymmetric carbons in some cases, it may exist in the form of optical isomers such as (R) form and (S) form, racemic modification, diastereomers and the like, based on the asymmetiric carbon. Also, depending on the type of substituents, it may exist in geometrical isomer forms such as (Z) form and (E) form based on the presence of double bond. All of these isomers in separated forms or mixtures thereof are included in the present invention.

Certain members of the compound (I) of the present invention can form salts with acids. Examples of such salts include acid addition salts with an inorganic acid (e.g., hydrochloric acid, hydrobromic acid, hydroiodic acid, sulfuric acid, nitric acid, phosphoric acid and the like) and with an organic acid (e.g., formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid and the like). In addition, the compound (I) of the present invention may be isolated in the form of hydrates, solvates with ethanol and the like or as a substance having polymorphism.

(Production Methods)

The compound (I) of the present invention can be produced by employing various production methods. The following describes typical production methods.

First production method

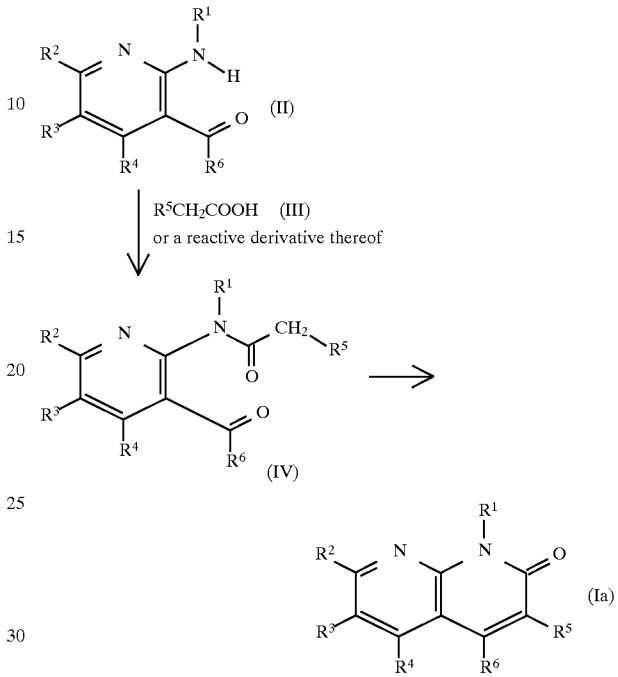

(In the above formulae, $R^1$, $R^2$, $R^3$, $R^4$, $R^5$ and $R^6$ are as defined in the foregoing.)

This method comprises a first step to produce an amide derivative (IV) from an aminopyridine derivative (II) and a second step to produce a compound (Ia) of the present invention from the amide derivative (IV).

In the first step, the amide derivative (IV) is obtained by allowing the aminopyridine derivative (II) to react with a carboxylic acid derivative represented by the general formula (III).

Examples of the carboxylic acid derivative represented by the general formula (III) include acid anhydrides; usual esters such as methyl ester, ethyl ester and the like of carboxylic acids; acid halides such as acid chloride, acid bromide and the like; acid azides; active esters obtained by reaction with a phenolic compound such as p-nitrophenol or the like or with an N-hydroxylamine compound such as 1-hydroxysuccinimide, 1-hydroxybenzotriazole or the like; and mixed acid anhydrides such as an organic acid-based mixed acid anhydrides obtained by reaction with halocarboxylic acid alkyl ester (e.g., an alkyl carbonic acid halide), pivaloyl halide, and the like, or a phospholic acid-based mixed acid anhydrides obtained by reaction with diphenylphosphoryl chloride, N-methylmorpholine and the like.

When a carboxylic acid is allowed to undergo the reaction as a free acid or an active ester is allowed to undergo the reaction without isolation, it is desirable to use a condensing agent such as dichlorohexylcarbodiimide, carbonyldiimidazole, diphenylphosphoryl azide, diethylphosphoryl cyanide, 1-ethyl-3-(3-dimethylaminopropyl) carbodiimide hydrochloride or the like.

According to the present invention, it is particularly advantageous to employ the acid anhydride method, the acid chloride method, a method in which the reaction is carried out in the presence of an active ester and a condensing agent or a method in which an usual ester is treated with an amine, because the compound of the present invention can be obtained simply and easily.

The amidation reaction is carried out in an inert organic solvent which includes halogenated hydrocarbons (e.g., dichloromethane, dichloroethane, chloroform and the like), aromatic hydrocarbons (e.g., benzene, toluene, xylene and the like), ethers (e.g., diethyl ether, tetrahydrofuran, dioxane and the like) and N,N-dimethylformamide and the like, or in the absence of solvent and, though it varies depending on the starting material, the condensing agent and the like to be used, at a cooling temperature of from −78° C. to 0° C., at a cooling temperature to room temperature, at room temperature or, as occasion demands, at room temperature to a heating temperature.

In the reaction, the aminopyridine derivative (II) and the carboxylic acid derivative represented by the general formula (III) may be used in the same molar level or one of them may be used in an excess amount, and, in some cases, it is advantageous for the smooth reaction to effect the reaction in the presence of a base such as N-methylmorpholine, trimethylamine, triethylamine, diisopropylethylamine, N,N-dimethylaniline, pyridine, 4-(N,N-dimethylamino)pyridine, dimethylaminopyridine, picoline, lutidine or the like. Pyridine can be used also as a solvent.

In the second step, the compound (I) of the present invention is obtained by subjecting the amide derivative (IV) to intramolecular aldol condensation. Similar to the case of usual aldol condensation, the reaction is carried out in the presence of an acid or a base at a cooling temperature of from −78° C. to 0° C., at a cooling temperature to room temperature, at room temperature or, as occasion demands, at room temperature to a heating temperature. This reaction is carried out in a solvent inert to the reaction, such as benzene, toluene, xylene, ether, tetrahydrofuran, dioxane or the like.

Since there is a possibility of forming an acid addition salt in the presence of an acid, it is desirable to carry out the reaction in the presence of a catalytically effective amount, equivalent mole or, as occasion demands, excess amount of a base. Examples of useful bases include alkali metal alkoxides (e.g., potassium tert-butoxide, sodium methoxide and the like), alkali metals (e.g., sodium and the like), alkali metal hydrides (e.g., sodium hydride, potassium hydride and the like), alkyl metals (e.g., butyl lithium and the like) and alkali metal amides (e.g., sodium amide, lithium amide, lithium diisopropylamide, lithium hexamethyldisilazide and the like).

Alternatively, this reaction may be carried out in an alcohol solvent such as methanol, ethanol or the like using a base such as an alkali metal alkoxide, sodium hydroxide, potassium hydroxide or the like.

Second production method

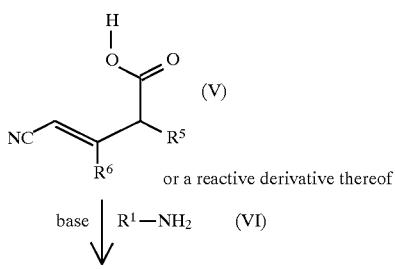

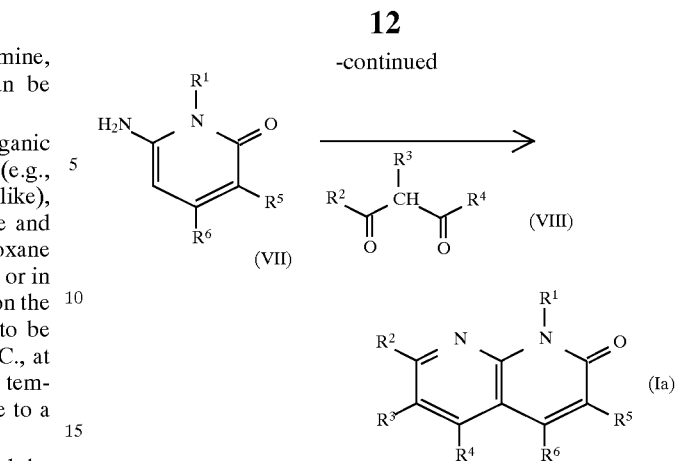

(In the above formulae, $R^1$, $R^2$, $R^3$, $R^4$, $R^5$ and $R^6$ are as defined in the foregoing.)

This method comprises a first step in which a pyridone derivative (VII) is produced from a cyanobutenoic acid derivative represented by the general formula (V) and a second step in which a compound (Ia) of the present invention is produced from the pyridone derivative (VII).

In the first step, the pyridone derivative (VII) is obtained by effecting cyclization of the cyanobutenoic acid derivative represented by the general formula (V) in the presence of a primary amine (VI).

Examples of the cyanobutenoic acid derivative represented by the general formula (V) include acid anhydrides; usual esters (e.g., methyl ester, ethyl ester and the like) of cyanobutenoic acid; acid halides such as acid chloride, acid bromide and the like; acid azides; active esters obtained by reaction with a phenolic compound such as p-nitrophenol or the like or with an N-hydroxylamine compound such as 1-hydroxysuccinimide, 1-hydroxybenzotriazole or the like; and mixed acid anhydrides such as an organic acid-based mixed acid anhydrides obtained by reaction with halocarboxylic acid alkyl ester (e.g., an alkyl carbonic acid halide), pivaloyl halide, and the like, or a phospholic acid-based mixed acid anhydride obtained by reaction with diphenylphosphoryl chloride, N-methylmorpholine and the like.

When a cyanobutenoic acid is allowed to undergo the reaction as a free acid or an active ester is allowed to undergo the reaction without isolation, it is desirable to use a condensing agent such as dichlorohexylcarbodiimide, carbonyldiimidazole, diphenylphosphoryl azide, diethylphosphoryl cyanide, 1-ethyl-3-(3-dimethylaminopropyl)carbodiimide hydrochloride or the like.

According to the present invention, it is particularly advantageous to employ the acid anhydride method, the acid chloride method, a method in which the reaction is carried out in the presence of an active ester and a condensing agent or a method in which an usual ester is treated with an amine, because the compound of the present invention can be obtained simply and easily.

It is desirable to carry out this reaction in the presence of a base. Examples of the useful bases include alkali metals (e.g., sodium and the like), alkali metal alkoxides (e.g., potassium tert-butoxide, sodium methoxide and the like) and alkali metal hydrides (e.g., sodium hydride and the like).

As the solvent, organic solvents are generally used, which include alcohol solvents (e.g., methanol, ethanol and the like), aromatic hydrocarbons (e.g., benzene, toluene, xylene and the like), ethers (e.g., diethyl ether, tetrahydrofuran and the like) and N,N-dimethylformamide, dimethyl sulfoxide and the like.

Though it varies depending on the starting material, the base, etc. to be used, this reaction is carried out at a cooling temperature, at a cooling temperature to room temperature or, as occasion demands, at room temperature to a heating temperature.

In the second step, the compound (Ia) of the present invention is obtained by the reaction of the pyridone derivative (VII) with a β-diketone (VIII). This reaction may be carried out using the compound (VII) and compound (VIII) in equivalent molar ratio, or one of them in an excess amount, under an acidic condition of sulfuric acid, trifluoroacetic acid, trifluoromethanesulfonic acid, trifluoroacetic anhydride, trifluoromethanesulfonic anhydride, 85% phosphoric acid, phosphoric anhydride or the like, preferably in polyphosphoric acid, under ice-cooling, at room temperature or, as occasion demands, at a heating temperature. Alternatively, this reaction may be carried out in an organic solvent inert to the reaction, such as benzene, toluene or the like, in the presence of a Lewis acid such as aluminum chloride, stannic chloride, boron trifluoride etherate or the like.

Third production method

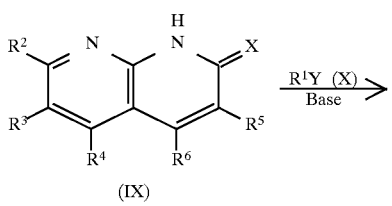

(In the above formulae, $R^1$, $R^2$, $R^3$, $R^4$, $R^5$, $R^6$ and X are as defined in the foregoing, and Y represents a leaving group advantageous for this reaction.)

In this method, the compound (I) of the present invention is produced by allowing a compound (IX) to react with a compound (X).

Examples of the leaving group represented by Y include halogen atoms (e.g., iodine atom, bromine atom, chlorine atom and the like) and organic sulfonic acid residues such as alkyl sulfonyloxy groups (e.g., methanesulfonyloxy group, ethanesulfonyloxy group and the like) and aryl sulfonyloxy groups (e.g., benzenesulfonyloxy group, toluene (particularly p-toluene)sulfonyloxy group and the like).

This reaction can be carried out using the compound (IX) and the compound (X) in equivalent molar basis, or one of them in an excess amount, in an organic solvent which is inert to the reaction, such as benzene, ether, tetrahydrofuran, dioxane, dimethylformamide, dimethyl sulfoxide or the like, in the presence of a base, at a cooling temperature of from −78° C. to 0° C., at room temperature or, as occasion demands, at a heating temperature. Examples of useful bases include sodium hydride, potassium hydride, lithium diisopropylamide, lithium hexamethyldisilazide, sodium methoxide, potassium tert-butoxide and the like. Alternatively, this reaction may be carried out in an alcohol solvent such as methanol, ethanol or the like using a base such as sodium alcolate, potassium alcolate, sodium hydroxide, potassium hydroxide or the like.

Fourth production method

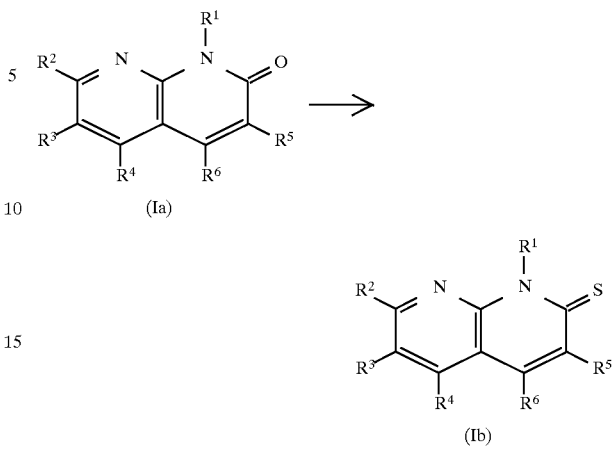

(In the above formulae, $R^1$, $R^2$, $R^3$, $R^4$, $R^5$ and $R^6$ are as defined in the foregoing.)

In this method, a compound of the present invention (Ib) in which X is sulfur atom is obtained by allowing another compound of the present invention (Ia) in which X is oxygen atom to react with phosphorus pentasulfide, Lawesson reagent or the like.

This reaction can be carried out using the compound (Ia) and phosphorus pentasulfide or Lawesson reagent in equivalent molar basis, or one of them in an excess amount, in an organic solvent which is inert to the reaction, such as benzene, toluene, tetrahydrofuran, ether, dioxane, methylene dichloride or the like, at room temperature or, as occasion demands, at a heating temperature.

Other production methods

Among compounds of the present invention, a compound in which one of $R^2$, $R^3$, $R^4$, A group, B group and C group is amino group can be obtained by reducing a corresponding compound of the present invention in which the substituent is nitro group. Illustratively, it can be obtained by carrying out hydrogenation of a compound of the present invention in which one of $R^2$, $R^3$, $R^4$, A group, B group and C group is nitro group, at room temperature or at a heating temperature, in an organic solvent inert to the reaction, such as methanol, ethanol, ethyl acetate, diethyl ether, acetic acid or the like and in the presence of a catalyst (e.g., Raney nickel, palladium-carbon, palladium, platinum oxide, palladium hydroxide or the like).

Alternatively, it can be obtained by effecting reduction of the compound of the present invention in which one of $R^2$, $R^3$, $R^4$, A group, B group and C group is nitro group, in a protic solvent such as water, methanol, ethanol or the like or a mixed solvent thereof in the presence of the equivalent molar ratio or excess amount of a metal such as iron powder, tin, zinc or the like, at a temperature of from cooling to room temperature or, as occasion demands, at a heating temperature.

Among the compounds of the present invention, a compound of the present invention in which one of $R^2$, $R^3$, $R^4$ and C group is a hydroxyl group can be obtained by effecting dealkylation of a compound in which the corresponding substituent is a lower alkoxy group. Illustratively, it can be obtained by allowing the compound of the present invention in which one of $R^2$, $R^3$, $R^4$ and C group is a lower alkoxy group to react with Lewis acid such as boron tribromide, aluminum chloride, titanium tetrachloride or the like. The reaction is carried out in a solvent which is inert to the reaction (e.g., dichloromethane, benzene or the like), at a cooling temperature of from −78° C. to 0° C., at a cooling temperature to room temperature, at room temperature or, as occasion demands, at a temperature of from room temperature to a heating temperature. Alternatively, it can be obtained by allowing the compound of the present invention in which one of $R^2$, $R^3$, $R^4$ and C group is a lower alkoxy group to undergo reaction with a mineral acid such as hydrochloric acid, hydrobromic acid, hydroiodic acid or the like. The reaction can be carried out under ice-cooling, at room temperature or, as occasion demands, with heating.

On the other hand, the compound of the present invention in which one of $R^2$, $R^3$, $R^4$ and C group is a hydroxyl group can also be obtained from its precursor in which the hydroxyl group is protected, by effecting its deprotection. As the protecting group, a substituted benzyl group such as benzyl, paramethoxybenzyl, paranitrobenzyl or the like, an acyl group such as formyl, acetyl, pivaloyl, benzoyl or the like, a tri-substituted silyl group such as trimethylsilyl, tert-butyldimethylsilyl, tert-butyldiphenylsilyl or the like, an ether group such as methoxymethyl, tetrahydropyranyl or the like may be used, and the protecting group is deprotected in a usual way, as the occasion demands, to obtain the compound of the present invention.

The resulting compound of the present invention is isolated and purified in a free form or as a salt thereof by subjecting it to a commonly used salt formation reaction. Isolation and purification are carried out by employing usual chemical treatments such as extraction, concentration, evaporation, crystallization, filtration, recrystallization, and various types of chromatography.

Various types of isomers can be isolated in the usual way making use of physicochemical differences among isomers. For example, a racemic compound is made into stereochemically pure isomers by a general racemic resolution method [for example, a method in which optical resolution is effected by leading it into a diastereomer salt with a general optically active acid (e.g., tartaric acid)]. Also, a diastereomer mixture can be separated by the commonly used means such as a fractional crystallization, a chromatography or the like.

In addition, an optically active compound can be produced by using an appropriate optically active starting material.

Industrial Applicability

The compounds (I) of the present invention have a type IV phosphodiesterase-inhibiting activity and are useful as an agent for the prevention or treatment of the following diseases in which type IV phosphodiesterase is concerned.

Respiratory diseases (e.g., bronchial asthma (including atopic asthma), chronic bronchitis, pneumonia, adult respiratory distress syndrome (ARDS) and the like), inflammatory diseases (e.g., atopic dermatitis, conjunctivitis, urticaria, acquired immunodeficiency syndrome (AIDS), keloid formation, rhinitis, iridocylitis, gingivitis, periodontitis, alveolar pyorrhea, gastritis, ulcerative colitis, Crohn disease, gastrointestinal ulcer, esophagitis, myositis, encephalitis (myasthenia gravis, multiple sclerosis and neuritis), hepatitis, cicatrization, nephritis (including proliferative nephritis), peritonitis, pleuritis, scleritis, scleroderma, burn injury and the like), systemic or local arthropathy (e.g., osteoarthrosis, gouty arthritis, chronic rheumatoid arthritis, malignant rheumatoid, psoriatic arthritis and the like), proliferative diseases (e.g., malignant tumor, leukemia, proliferative dermatopathy (keratosis and various types of dermatitis), collagen disease and the like), diseases related to nervous function abnormality (e.g., learning, memory and cognition disturbances related to nervous degeneration diseases such as Alzheimer disease, Parkinson disease and the like, multiple lateral sclerosis, senile dementia, amyotrophic lateral sclerosis, acute demyelinating neuritis, muscular dystrophy and the like), diseases with mental function abnormality (e.g., manic-depressive psychosis, schizoid, anxiety, panic and the like), inflammation due to organ transplantation and the like (e.g., reperfusion injury, graft versus host reaction and the like), diseases which require protection of nerves and cells (e.g., cardiac arrest, spinal cord injury, intermittent claudication, ischemic diseases (e.g., angina pectoris, myocardial infarction, stroke, head injury and the like) and the like), diseases related to micturition (e.g., diabetes insipidus, urethritis, urinary incontinence, cystitis, irritable bladder, neurogenic bladder, uremia, tubular disorder, pollakiuria, urinary retention and the like), endocrine diseases including diabetes mellitus (e.g., diabetic retinopathy, diabetic nephropathy, diabetic neuropathy, amyloidosis, pancreatitis, thyroiditis, obesity, prostatic hypertrophy and the like), diseases in which tumor necrosis factor (TNF) and other cytokine (IL-1, IL-6 and the like) are concerned (e.g., psoriasis, rheumatoid arthritis, ulcerative colitis, Crohn disease, sepsis, septic shock, endotoxin shock, Gram negative bacillus sepsis, toxic shock syndrome, nephritis, hepatitis, infection (bacterial and viral), circulatory failure (heart failure, arteriosclerosis, myocardial infarction, stroke) and the like), autoimmune diseases (e.g., systemic lupus erythematosus, atrophic gastritis, thyroid gland disease, glomerulonephritis, orchitis, adrenal disease, hemolytic anemia, oophoritis and the like), circulatory organ diseases (e.g., hypertension, angina pectoris, heart failure, myocarditis, epicarditis, endocarditis, valvulitis and the like), diseases of vascular and blood systems (e.g., angitis, aneurysm, vascular endothelial injury, thrombosis inflammation, granuloma, cerebrovascular inflammation, arteriosclerosis, perivascular inflammation, leukopenia, thrombocytopenia, sarcoidosis and the like), diseases in which immune allergy reactions are concerned (e.g., contact dermatitis, serum sickness, drug allergy, Goodpasture syndrome, lymphomatosis, rheumatic fever, AIDS, anaphylactic shock and the like), and other diseases [glaucoma, spastic paralysis, impotence, diseases with pain (e.g., contusion, headache and the like), cervico-omo-branchial syndrome, nephropathy, renal insufficiency, hepatic insufficiency and obesity).

The compound (I) of the present invention is useful for the prevention or treatment of respiratory diseases (e.g., bronchial asthma (including atopic asthma), chronic bronchitis, pneumonia, ARDS and the like), inflammatory diseases (e.g., atopic dermatitis, conjunctivitis, urticaria, acquired immunodeficiency syndrome (AIDS), keloid formation, rhinitis, iridocylitis, gingivitis, periodontitis, alveolar pyorrhea, gastritis, ulcerative colitis, Crohn disease, gastrointestinal ulcer, esophagitis, myositis, encephalitis (myasthenia gravis, multiple sclerosis and neuritis), hepatitis, cicatrization, nephritis (including proliferative nephritis), peritonitis, pleuritis, scleritis, scleroderma, burn injury and the like), and diseases in which tumor necrosis factor (TNF) and other cytokine (IL-1, IL-6 and the like) are concerned (e.g., psoriasis, rheumatoid arthritis, ulcerative colitis, Crohn disease, sepsis, septic shock, endotoxin shock, Gram negative bacillus sepsis, toxic shock syndrome, nephritis, hepatitis, infection (bacterial and viral), circulatory failure (heart failure, arteriosclerosis, myocardial infarction, stroke) and the like).

Also, since the compounds of the present invention show extremely weak vomiting action in comparison with the prior type IV phosphodiesterase inhibitors, they are particularly useful for the treatment or prevention of diseases in patients who require systemic administration.

Activities of the compounds of the present invention to inhibit types I, II, III, IV and V phosphodiesterase were confirmed by the following tests.

Phosphodiesterase Inhibition Activity Measuring Test (in vitro)

(1) Method for measuring type IV phosphodiesterase inhibition activity

The following assay was used for the evaluation of the capability of the compounds of the present invention to inhibit type IV phosphodiesterase.

1) Physiological saline (200 ml) supplemented with dextran (3%) was added to 500 ml of heparinized peripheral blood of a healthy person and incubated at 37° C. for 40 minutes to effect precipitation of erythrocytes. The supernatant after precipitation of erythrocytes was recovered and centrifuged once, and the resulting precipitate was suspended in buffer A (140 mM NaCl, 5 mM KCl, 5 mM glucose and 10 mM HEPES, pH 7.4), overlaid on a solution for density gradient centrifugation use (Ficoll solution) and then centrifuged at room temperature for 40 minutes at 450×g, thereby separating monocyte fraction and granulocyte fraction. The granulocyte fraction was washed once with buffer B (140 mM NaCl, 5 mM KCl, 1 mM CaCl$_2$, 1 mM MgCl$_2$, 5 mM glucose and 10 mM HEPES, pH 7.4) and suspended in buffer C (20 mM Bis-Tris, 5 mM dithioerythritol, 2 mM EGTA and 50 mM sodium acetate, pH 6.5) containing a protease inhibitor (50 µM phenyl-methyl-sulfonyl-fluoride, 5 µM pepstatin A, 40 µM leupeptin, 20 µM aprotinin or 2 mM benzamidine) and then the cells were disrupted using polytron and sonicator and subjected to ultracentrifugation (4° C., 100,000×g, 60 minutes) to give a soluble fraction.

2) The thus obtained soluble fraction was applied to a column of 1.6×10 cm packed with Q Sepharose which had been equilibrated with buffer C. Next, the column was washed with 300 ml of buffer C to remove non-absorbed protein. Phosphodiesterase was eluted with 200 ml of buffer C having 0.05 to 1.25M linear gradient of sodium acetate to collect 40 fractions each containing 5.0 ml eluate. Each fraction was checked for cAMP- and cGMP-metabolizing phosphodiesterase activities. Fractions having no cGMP- but cAMP-metabolizing activity and showing disappearance of the metabolizing activity by 10 µM rolipram (a type IV phosphodiesterase selective inhibitor) were collected to be used as a stock solution for the examination of type IV phosphodiesterase inhibition activity.

3) A predetermined amount of each compound to be tested was subjected to 10 minutes of reaction at 30° C. in a reaction mixture containing 40 mM Tris-HCl (pH 8.0), 5 mM MgCl$_2$, 4 mM 2-mercaptoethanol, 0.3 µM cilostamide (a type III phosphodiesterase selective inhibitor), 1 µM cAMP, 10 nM $^3$H-cAMP and the type IV phosphodiesterase stock solution. The reaction solution was boiled at 90° C. for 1 minute, ice-cooled, mixed with 1 unit of 5'-nucleotidase and then subjected to 10 minutes of reaction at 30° C., and the reaction was stopped by the addition of 1 ml of methanol. The reaction solution was passed through a Dowex 1×8 column to adsorb un-hydrolyzed material and then the radioactivity was measured.

4) Concentration of each compound to be tested which inhibits 50% of the metabolic activity of type IV phosphodiesterase was calculated and expressed as IC$_{50}$. (2) Method for measuring the activity to inhibit various phosphodiesterase isozymes (A) In order to evaluate selectivity of the compounds of the present invention for type IV phosphodiesterase, types I, II, III and V phosphodiesterase isozymes were purified in the following manner.

1) Solutions containing various phosphodiesterase (types I, II and III) isozymes were purified from rat heart muscle cells in the following manner. Under ether anesthesia, Wistar rat was subjected to thoracotomy to excise the heart. After removing blood by perfusion with physiological saline supplemented with heparin (1 unit/ml), the heart was finely chopped with scissors. This was suspended in buffer A (20 mM Bis-Tris, 5 mM dithioerythritol, 2 mM EGTA and 50 mM sodium acetate, pH 6.5) containing a protease inhibitor (50 µM phenyl-methyl-sulfonyl-fluoride, 5 µM pepstatin A, 40 µM leupeptin, 20 µM aprotinin or 2 mM benzamidine) and then the cells were disrupted using polytron and sonicator and subjected to ultracentrifugation (4° C., 100,000×g, 60 minutes) to give a soluble fraction.

2) Solutions containing various phosphodiesterase isozymes were obtained from the thus obtained soluble fraction in the following manner. The thus, obtained soluble fraction was applied to a column of 1.6×10.0 cm packed with Q Sepharose which had been equilibrated with buffer A. Next, said column was washed with 300 ml of buffer A to remove non-absorbed protein. Phosphodiesterase was eluted with 200 ml of buffer A having 0.05 to 1.25M linear gradient of sodium acetate to collect about 40 fractions each containing 5.0 ml eluate. Each fraction was checked for cAMP- and cGMP-metabolizing phosphodiesterase activities. Of these fractions, a fraction having only cAMP-metabolizing activity and showing disappearance of the metabolizing activity by 0.1 µM cilostamide (a type III phosphodiesterase selective inhibitor) was used as the type III phosphodiesterase. Also, a fraction which showed increased cAMP metabolizing activity by the addition of 2 µM cGMP was used as the II type phosphodiesterase. In addition, a fraction which did not show changes in the cAMP metabolizing activity by the addition of cGMP but the cAMP metabolizing activity was increased by the addition of 2 mM CaCl$_2$ was used as the type I phosphodiesterase. These fractions were separately collected to be used as phosphodiesterase (types I, II and III) stock solutions for the examination of selectivity. p1 3) A solution containing type V phosphodiesterase was prepared from peripheral blood of a healthy person in the following manner. A 200 ml portion of physiological saline supplemented with dextran (3%) was added to 500 ml of heparinized peripheral blood and incubated at 37° C. for 40 minutes to effect precipitation of erythrocytes. The supernatant fluid after precipitation of erythrocytes was recovered and centrifuged once, and the resulting precipitate was suspended in buffer B (140 mM NaCl, 5 mM KCl, 5 mm glucose and 10 mM HEPES, pH 7.4), overlaid on a solution for density gradient centrifugation use (Ficoll solution) and then centrifuged at room temperature for 40 minutes at 450×g, thereby separating monocyte fraction and granulocyte fraction. The granulocyte fraction was washed once with buffer C (140 mM NaCl, 5 mM KCl, 1 mM $CaCl_2$, 1 mM $MgCl_2$, 5 mM glucose and 10 mM HEPES, pH 7.4) and suspended in buffer D (20 mM Bis-Tris, 5 mM dithioerythritol, 2 mM EGTA and 50 mM sodium acetate, pH 6.5) containing a protease inhibitor (40 $\mu$M leupeptin, 5 $\mu$M pepstatin A, 20 $\mu$M aprotinin, 50 $\mu$M phenyl-methyl-sulfonyl-fluoride or 2 mM benzamidine) and then the cells were disrupted using polytron and sonicator and subjected to ultracentrifugation (4° C., 100,000×g, 60 minutes) to give a soluble fraction.

4) The thus obtained soluble fraction was applied to a column of 1.6×10 cm packed with Q Sepharose which had been equilibrated with buffer D. Next, the column was washed with 120 ml of buffer D to remove non-absorbed protein. Phosphodiesterase was eluted with 300 ml of buffer D having 0.05 to 1.25M linear gradient of sodium acetate to collect fractions each containing 5.0 ml eluate. Each fraction was checked for cAMP- and cGMP-metabolizing phosphodiesterase activities. Fractions having only cGMP metabolizing activity were collected to be used as the type V phosphodiesterase stock solution.

(B) Inhibitory activities were measured using the thus obtained stock solutions of various phosphodiesterase isozymes.

1) A predetermined amount of each compound to be tested was subjected to 10 minutes of reaction at 30° C. in a reaction mixture containing 40 mM Tris-HCl (pH 8.0), 5 mM $MgCl_2$, 4 mM 2-mercaptoethanol, 10 $\mu$M rolipram (a type IV phosphodiesterase selective inhibitor), 1 $\mu$M cAMP, 10 nM $^3$H-cAMP (in the case of type V phosphodiesterase, 1 $\mu$M cAMP and 10 nM $^3$H-cAMP are replaced by 1 $\mu$M cGMP and 100 nM $^3$H-cGMP) and each of the isozyme stock solutions. After completion of the reaction, the reaction mixture was boiled at 90° C. for 1 minute, ice-cooled, mixed with 1 unit of 5'-nucleotidase and then subjected to 10 minutes of reaction at 30° C., and the reaction was stopped by adding 1 ml of methanol. The reaction solution was passed through a Dowex 1×8 column to effect adsorption of un-metabolized cAMP or cGMP and then radioactivity in the eluate was measured using a scintillation counter.

2) The $IC_{50}$ value of each compound to be tested was calculated as a concentration of the compound which inhibits 50% of the metabolic activity of each of the isozymes, and selectivity of the inhibition activity ($IC_{50}$) was evaluated.

Results: The inhibition activity ($IC_{50}$) value for h type of phosphodiesterase (Type I, Type II, Type III, e IV, and Type V) is shown in the following table.

| Compound | $IC_{50}$ ($\mu$M) | | | | |
|---|---|---|---|---|---|
| | Type I | Type II | Type III | Type IV | Type V |
| Example 15 | 0.0338 | 20.8 | 50.3 | 58.9 | 41.2 |
| Example 24 | 0.0419 | 51.8 | 21.5 | 98.3 | 9.7 |
| Example 26 | 0.0234 | 30.0 | 56.2 | 84.9 | 27.3 |
| Example 27 | 0.0213 | 25.6 | 15.5 | >30 | 27.9 |
| Example 29 | 0.0116 | 15.5 | 14.3 | >30 | 24.6 |
| Example 30 | 0.0099 | 10.5 | 10.9 | 31.2 | 8.66 |
| Example 31 | 0.0043 | >30 | >30 | >30 | >30 |
| Example 33 | 0.0143 | 35.4 | 17.7 | >30 | 8.39 |
| Example 35 | 0.0242 | 22.3 | 34.4 | 21.9 | 41.6 |
| Example 38 | 0.0124 | 26.1 | >30 | >30 | 19.6 |
| Example 39 | 0.0025 | >3 | >3 | >3 | 1.05 |
| Example 40 | 0.0129 | 20.5 | 32.3 | 31.9 | 14.5 |
| Example 43 | 0.0160 | >30 | >30 | >30 | 4.79 |
| Example 46 | 0.0389 | >30 | >30 | >30 | 87.0 |
| Example 49 | 0.0337 | 22.8 | 27.3 | 30.2 | 3.87 |
| Comparative Compound A | 0.250 | >30 | >30 | >30 | 31.5 |

Comparative compound A: Example 1 in International Publication 94/12499

As is evident from the results of the above tests (1) and (2), the compound (I) of the present invention has a potent activity to inhibit type IV phosphodiesterase and is also excellent in the selectivity.

Test for the measurement of carrageenin pleurisy inhibition ratio (in vivo)

Carrageenin pleurisy was induced by percutaneous administration of 100 $\mu$l of 1% (w/v) carrageenin-purified water into the chest cavity of male Wistar rat of 5 to 7 weeks of age under ether anesthesia.

Each of the test compounds was suspended in 0.5% methylcellulose-purified water and orally administered 30 minutes before the induction. In this case, solvent (0.5% methylcellulose-purified water) was administered to the control group animals in the same manner.

After 4 hours of the induction, each animal was sacrificed by over-anesthesia and subjected to ventrotomy, and the chest cavity was washed with 1 ml of physiological saline to recover infiltrated leukocytes. The infiltrated leukocyte count in the thus recovered solution was measured using a blood cell counter (Celltac $\alpha$: Nihon Kohden Corp.)

The inhibition ratio by the test compounds was calculated based on the following expression.

$$\text{Inhibition ratio} = \frac{\frac{\text{infiltrated leukocyte count in compound-administered group}}{\text{infiltrated leukocyte count in solvent-administered group}} - \frac{\text{infiltrated leukocyte count in carrageenin-untreated group}}{\text{infiltrated leukocyte count in carrageenin-untreated group}}} \times 100$$

Inhibition ratios when each test compound was orally administered in a dose of 30 mg/kg were compared. Result: As a result of the measurement by this test method, the compound (I) of the present invention showed a carrageenin pleurisy inhibition ratio of 12.5% to 62.2%.

As the results of the aforementioned tests for the measurement of phosphodiesterase inhibition activity (in vitro) and carrageenin pleurisy inhibition ratio (in vivo), it was confirmed that the compound (I) of the present invention has an activity to selectively inhibit type IV phosphodiesterase and shows excellent inhibition effect in the in vivo oral administration test.

A pharmaceutical preparation which contains one or a plurality of the compounds of the present invention or salts thereof as the active ingredient is prepared using carriers, excipients and other additive agents generally used in the preparation of pharmaceuticals.

As the carriers and excipients for use in the pharmaceuticals, solid or liquid non-toxic substances for pharmaceutical use can be exemplified. The illustrative examples include lactose, magnesium stearate, starch, talc, gelatin, agar, pectin, gum arabic, olive oil, sesame oil, cacao butter, ethylene glycol and other commonly used substances.

It can be administered by oral administration in the dosage form of tablets, pills, capsules, granules, powders, solutions and the like or by parenteral administration in the form of injections (e.g., intravenous, intramuscular and the like), suppositories, transdermal preparations, inhalants and the like or by intravesical injection. The dose is optionally decided case by case taking symptoms, age, sex and the like of each patient into consideration, and it may be generally from about 0.001 mg/kg to about 100 mg/kg per day per adult in the case of oral administration, and the daily dose may be used once a day or divided into 2 to 4 doses per day. When administered by intravenous injection due to the symptoms, it may be administered once a day or a plurality of doses a day generally within the range of from 0.001 mg/kg to 10 mg/kg per adult. Also, in the case of inhalation, it may be administered once a day or a plurality of doses a day generally within the range of from 0.0001 mg/kg to 1 mg/kg per adult, or, in the case of application, it may be administered once a day or a plurality of doses a day generally within the range of from 0.0001 mg/kg to 1 mg/kg per adult.

Tablets, powders, granules and the like are used as the solid composition of the present invention for oral administration. In such a solid composition, one or more of the active substances are mixed with at least one inert diluent such as lactose, mannitol, glucose, hydroxypropylcellulose, microcrystalline cellulose, starch, polyvinyl pyrrolidone or aluminum magnesium matasilicate. In accordance with the conventional way, the composition may further contain additive agents other than the inert diluent, such as lubricants (e.g., magnesium stearate or the like), disintegrators (e.g., calcium cellulose glycolate or the like), stabilizers (e.g., lactose or the like) and solubilizing agents (e.g., glutamic acid, aspartic acid or the like). As occasion demands, tablets or pills may be coated with films of a gastric or enteric substance such as sucrose, gelatin, hydroxypropylcellulose or hydroxypropylmethylcellulose phthalate.

The liquid composition for oral administration includes pharmaceutically acceptable emulsions, solutions, suspensions, syrups, elixirs and the like, and contains commonly used inert diluent such as purified water or ethanol. In addition to the inert diluent, this composition may also contain auxiliary agents such as moistening agents, suspending agents and the like, sweeteners, flavors, aromas and antiseptics.

The injections for parenteral administration include aseptic aqueous or non-aqueous solutions, suspensions and emulsions. Distilled water for injection, physiological saline and the like are used in the aqueous solutions and suspensions. Propylene glycol, polyethylene glycol, plant oils (e.g., olive oil and the like), alcohols (e.g., ethanol and the like), polysorbate 80 and the like are used in the non-aqueous solutions and suspensions. These compositions may also contain auxiliary agents such as antiseptics, moistening agents, emulsifying agents, dispersing agents, stabilizing agents (e.g., lactose) and solubilizing agents (e.g., glutamic acid and aspartic acid). These compositions are sterilized, for example, by filtration through a bacteria retaining filter, blending of a germicide or irradiation. Also, these compositions may be produced as aseptic solid compositions, which are used by dissolving in sterile water or a sterile solvent for injection prior to their use.

BEST MODE OF CARRYING OUT THE INVENTION

The following describes the present invention further in detail with reference to Examples. The present invention is not limited to the compounds described in the following Examples, and all of the compounds represented by the aforementioned general formula (I), salts thereof, hydrates thereof, solvates thereof, geometrical and optical isomers thereof and polymorphic forms thereof are included therein.

In the Examples and Reference Examples, nuclear magnetic resonance spectrum was measured at 400 MHz and at room temperature.

REFERENCE EXAMPLE 1

Acetic anhydride (40 ml) solution containing 3-(3-chlorobenzoyl)-2-methylaminopyridine (3.16 g, 13 mmol) was heated under reflux for 4 hours. The reaction solution was concentrated under reduced pressure, and the resulting residue was purified by silica gel column chromatography (benzene-ethyl acetate) to give N-[3-(3-chlorobenzoyl)-2-pyridyl]-N-methylacetamide (3.34 g, 90%).

Mass spectrometry data (m/z): 288 ($M^+$)

Nuclear magnetic resonance spectrum ($CDCl_3$, TMS internal standard) δ: 2.00 (3H, br), 3.05, 3.51 (3H, br×2), 7.20–8.00 (6H, m), 8.62 (1H, br).

The following compounds of Reference Examples 2 to 22 were obtained in the same manner as described in Reference Example 1.

REFERENCE EXAMPLE 2

N-(3-Benzoyl-2-pyridyl)-N-methylacetamide

Starting compound: 3-benzoyl-2-methylaminopyridine

Mass spectrometry data (m/z): 254 ($M^+$)

Nuclear magnetic resonance spectrum ($CDCl_3$, TMS internal standard) δ: 1.93 (3H, br), 3.05, 3.48 (3H, br×2), 7.2–7.9 (7H, m), 8.63 (1H, br).

REFERENCE EXAMPLE 3

N-[3-(3-Methylbenzoyl)-2-pyridyl]-N-methylacetamide

Starting compound: 3-(3-methylbenzoyl)-2-methylaminopyridine

Mass spectrometry data (m/z): 268 ($M^+$)

Nuclear magnetic resonance spectrum ($CDCl_3$, TMS internal standard) δ: 1.93 (3H, br), 2.40 (3H, s), 3.03, 3.47 (3H, br×2), 7.3–7.9 (6H, m), 8.65 (1H, br).

REFERENCE EXAMPLE 4

N-Methyl-N-[3-(2-methylbenzoyl)-2-pyridyl]acetamide

Starting compound: 2-methylamino-3-(2-methylbenzoyl)pyridine

Mass spectrometry data (m/z): 268 ($M^+$)

Nuclear magnetic resonance spectrum ($CDCl_3$, TMS internal standard) δ: 1.87 (3H, s), 2.53 (3H, s), 2.92, 3.35 (3H, br×2), 7.18–7.39 (5H, m), 7.88 (1H, br), 8.60 (1H, br).

REFERENCE EXAMPLE 5

N-[3-(3-Methoxybenzoyl)-2-pyridyl]-N-methylacetamide

Starting compound: 3-(3-methoxybenzoyl)-2-methylaminopyridine

Mass spectrometry data (m/z): 284 ($M^+$)

Nuclear magnetic resonance spectrum ($CDCl_3$, TMS internal standard) δ: 1.97 (3H, br), 3.07, 3.48 (3H, br×2), 3.85 (3H, s), 7.1–7.5 (5H, m), 7.82 (1H, br), 8.63 (1H, br).

REFERENCE EXAMPLE 6

N-[3-(4-Chlorobenzoyl)-2-pyridyl]-N-methylacetamide

Starting compound: 3-(4-chlorobenzoyl)-2-methylaminopyridine

Mass spectrometry data (m/z): 288 (M$^+$)

Nuclear magnetic resonance spectrum (CDCl$_3$, TMS internal standard) δ: 2.03 (3H, br), 3.05, 3.51 (3H, br×2), 7.2–7.9 (6H, m), 8.61 (1H, br).

REFERENCE EXAMPLE 7

N-[3-(3-Bromobenzoyl)-2-pyridyl]-N-methylacetamide

Starting compound: 3-(3-bromobenzoyl)-2-methylaminopyridine

Mass spectrometry data (m/z): 332, 334 (M$^+$)

Nuclear magnetic resonance spectrum (CDCl$_3$, TMS internal standard) δ: 1.99 (3H, br), 3.05, 3.51 (3H, br×2), 7.2–8.1 (6H, m), 8.62 (1H, br).

REFERENCE EXAMPLE 8

N-[3-(2,3-Dichlorobenzoyl)-2-pyridyl]-N-methylacetamide

Starting compound: 3-(2,3-dichlorobenzoyl)-2-methylaminopyridine

Mass spectrometry data (m/z): 322 (M$^+$)

Nuclear magnetic resonance spectrum (CDCl$_3$, TMS internal standard) δ: 1.88 (3H, br), 2.96, 3.37 (3H, br×2), 7.2–7.7 (4H, m), 7.9–8.1 (1H, m), 8.6–8.8 (1H, m).

REFERENCE EXAMPLE 9

N-[3-(3,5-Dichlorobenzoyl)-2-pyridyl]-N-methylacetamide

Starting compound: 3-(3,5-dichlorobenzoyl)-2-methylaminopyridine

Mass spectrometry data (m/z): 322 (M$^+$)

Nuclear magnetic resonance spectrum (CDCl$_3$, TMS internal standard) δ: 1.80–2.10 (3H, m), 3.00–3.60 (3H, m), 7.20–8.00 (5H, m), 8.62 (1H, br).

REFERENCE EXAMPLE 10

N-[3-(3-Trifluoromethyl)benzoyl-2-pyridyl]-N-methylacetamide

Starting compound: 3-(3-trifluoromethyl)benzoyl-2-methylaminopyridine

Mass spectrometry data (m/z): 322 (M$^+$)

Nuclear magnetic resonance spectrum (CDCl$_3$, TMS internal standard) δ: 1.97 (3H, br), 3.03, 3.51 (3H, br×2), 7.2–8.2 (6H, m) 8.63 (1H, br).

REFERENCE EXAMPLE 11

N-[3-(3-Cyanobenzoyl)-2-pyridyl]-N-methylacetamide

Starting compound: 3-(3-cyanobenzoyl)-2-methylaminopyridine

Mass spectrometry data (m/z): 279 (M$^+$)

Nuclear magnetic resonance spectrum (CDCl$_3$, TMS internal standard) δ: 2.04 (3H, br), 3.04, 3.55 (3H, br×2), 7.2–8.2 (6H, m), 8.63 (1H, br).

REFERENCE EXAMPLE 12

N-Methyl-N-[3-(3-nitrobenzoyl)-2-pyridyl]acetamide

Starting compound: 2-methylamino-3-(3-nitrobenzoyl)pyridine

Mass spectrometry data (m/z): 299 (M$^+$)

Nuclear magnetic resonance spectrum (CDCl$_3$, TMS internal standard) δ: 2.03 (3H, br), 3.09, 3.56 (3H, br×2), 7.26 (1H, br), 7.68 (2H, br), 8.19 (1H, br), 8.42 (1H, br), 8.64 (2H, br).

REFERENCE EXAMPLE 13

N-(3-Benzoyl-2-pyridyl)-N-methylpropionamide

Starting compound: 3-benzoyl-2-methylaminopyridine

Mass spectrometry data (m/z): 268 (M$^+$)

Nuclear magnetic resonance spectrum (CDCl$_3$, TMS internal standard) δ: 0.97 (3H, br), 2.12 (2H, br), 2.9–3.6 (3H, m), 7.2–7.9 (7H, m), 8.64 (1H, br).

REFERENCE EXAMPLE 14

N-(3-Benzoyl-2-pyridyl)-N-ethylacetamide

Starting compound: 3-benzoyl-2-ethylaminopyridine

Mass spectrometry data (m/z): 268 (M$^+$)

Nuclear magnetic resonance spectrum (CDCl$_3$, TMS internal standard) δ: 1.07, 1.39 (3H, br×2), 1.88, 2.06 (3H, br×2), 3.52, 4.00 (2H, br×2), 7.16–7.84 (7H, m), 8.58, 8.71 (1H, br×2).

REFERENCE EXAMPLE 15

N-[3-(3-Chlorobenzoyl)-2-pyridyl)-N-ethylacetamide

Starting compound: 3-(3-chlorobenzoyl)-2-ethylaminopyridine

Mass spectrometry data (m/z): 302 (M$^+$)

Nuclear magnetic resonance spectrum (CDCl$_3$, TMS internal standard) δ: 1.0–2.2 (6H, m), 3.51–4.04 (2H, br×2), 7.2–8.0 (6H, m), 8.5–8.8 (1H, m).

REFERENCE EXAMPLE 16

N-(3-Benzoyl-2-pyridyl)-N-propylacetamide

Starting compound: 3-benzoyl-2-propylaminopyridine

Mass spectrometry data (m/z): 282 (M$^+$)

Nuclear magnetic resonance spectrum (CDCl$_3$, TMS internal standard) δ: 0.78, 0.98 (3H, br×2), 1.40–2.20 (7H, m), 3.41, 3.89 (2H, br×2), 7.20–7.90 (7H, m), 8.57, 8.68 (1H, br×2).

REFERENCE EXAMPLE 17

N-(3-Benzoyl-2-pyridyl)-N-isopropylacetamide

Starting compound: 3-benzoyl-2-isopropylaminopyridine

Mass spectrometry data (m/z): 282 (M$^+$)

Nuclear magnetic resonance spectrum (CDCl$_3$, TMS internal standard) δ: 0.80–2.25 (9H, m), 4.25, 4.70 (1H, br×2), 7.20–8.00 (7H, m), 8.60–8.80 (1H, br).

REFERENCE EXAMPLE 18

N-(3-Benzoyl-2-pyridyl)-N-cyclopropylacetamide

Starting compound: 3-benzoyl-2-cyclopropylaminopyridine

Mass spectrometry data (m/z): 280 (M$^+$)

Nuclear magnetic resonance spectrum (CDCl$_3$, TMS internal standard) δ: 0.80 (2H, m), 0.94 (2H, m), 2.19 (3H, s), 3.05–3.10 (1H, m), 7.24–7.26 (1H, m), 7.45 (2H, t, J=7.3 Hz), 7.59 (1H, t, J=7.3 Hz), 7.68–7.69 (1H, m), 7.81 (2H, d, J=7.3 Hz), 8.64 (1H, dd, J=4.8, 1.8 Hz).

REFERENCE EXAMPLE 19

N-(3-Benzoyl-2-pyridyl)-N-cyclobutylacetamide

Starting compound: 3-benzoyl-2-cyclobutylaminopyridine

Mass spectrometry data (m/z): 294 (M$^+$)

Nuclear magnetic resonance spectrum (CDCl$_3$, TMS internal standard) δ: 1.57–2.26 (9H, m), 4.44–4.51 (1H, m), 7.33 7.95 (7H, m), 8.73 (1H, br).

REFERENCE EXAMPLE 20

N-(3-Benzoyl-2-pyridyl)-N-phenylacetamide
Starting compound: 3-benzoyl-2-phenylaminopyridine
Mass spectrometry data (m/z): 316 (M$^+$)
Nuclear magnetic resonance spectrum (CDCl$_3$, TMS internal standard) δ: 1.92 (3H, br), 7.20–7.60 (10H, m), 7.68 (1H, dd, J=7.3, 1.8 Hz), 8.54 (1H, br).

REFERENCE EXAMPLE 21

N-[3-(3-Nitrobenzoyl)-2-pyridyl]-N-(4-phenylbutyl) acetamide
Starting compound: 3-(3-nitrobenzoyl)-2 -(4-phenylbutyl)aminopyridine
Mass spectrometry data (m/z): 417 (M$^+$)
Nuclear magnetic resonance spectrum (CDCl$_3$, TMS internal standard) δ: 1.4–2.2 (7H, m), 2.5–2.7 (2H, m), 3.42, 4.05 (2H, br×2), 7.0–8.8 (12H, m).

REFERENCE EXAMPLE 22

N-(3-Benzoyl-2-pyridyl)-N-(2-pyridylmethyl) acetamide
Starting compound: 3-benzoyl-2-[(2-pyridylmethyl)amino]pyridine
Mass spectrometry data (m/z): 331 (M$^+$)
Nuclear magnetic resonance spectrum (CDCl$_3$, TMS internal standard) δ: 1.88, 2.04 (3H, br×2), 4.86, 5.29 (2H, br×2), 6.88–8.17 (11H, m), 8.54–8.70 (1H, m).

REFERENCE EXAMPLE 23

Ethyl 3-(3-bromophenyl)-4-cyano-3-butenoate (15 g, 50 mmol) and 28% ethylamine-methanol solution (20 ml) were added to a methanol (50 ml) solution of sodium (1.4 g, 60 mmol), and the mixture was allowed to stand overnight at room temperature. The reaction solution was poured into ice water and extracted with ethyl acetate. The ethyl acetate layer was dried over anhydrous magnesium sulfate, magnesium sulfate was removed by filtration and then the resulting filtrate was concentrated under reduced pressure. Thereafter, the resulting residue was purified by silica gel column chromatography (chloroform-methanol) to give 6-amino-4-(3-bromophenyl)-1-ethyl-2(1H)-pyridone (5.72 g, 38%).

Mass spectrometry data (m/z): 292, 294 (M$^+$)
Nuclear magnetic resonance spectrum (DMSO-d$_6$, TMS internal standard) δ: 1.14 (3H, t, J=6.7 Hz), 3.98 (2H, q, J=6.7 Hz), 5.64 (1H, d, J=1.8 Hz), 5.73 (1H, d, J=1.8 Hz), 6.61 (1H, s), 7.40 (1H, t, J=7.9 Hz), 7.55 (1H, d, J=7.9 Hz), 7.60 (1H, d, J=7.9 Hz), 7.68 (1H, d, J=1.8 Hz).

The following compounds of Reference Examples 24 to 27 were obtained in the same manner as described in Reference Example 23.

REFERENCE EXAMPLE 24

6-Amino-4-(3-chlorophenyl)-1-ethyl-2(1H)-pyridone
Starting compounds: ethyl 3-(3-chlorophenyl)-4-cyano-3-butenoate and ethylamine
Mass spectrometry data (m/z): 248 (M$^+$)
Nuclear magnetic resonance spectrum (DMSO-d$_6$, TMS internal standard) δ: 1.15 (3H, t, J=6.7 Hz), 4.00 (2H, q, J=6.7 Hz), 5.66 (1H, d, J=1.8 Hz), 5.75 (1H, d, J=1.8 Hz), 6.62 (2H, s), 7.47–7.55 (4H, m).

REFERENCE EXAMPLE 25

6-Amino-4-(3-chlorophenyl)-1-methyl-2 (1H)-pyridone
Starting compounds: ethyl 3-(3-chlorophenyl)-4-cyano-3butenoate and methylamine
Mass spectrometry data (m/z): 234 (M$^+$)
Nuclear magnetic resonance spectrum (DMSO-d$_6$, TMS internal standard) δ: 3.35 (3H, s), 5.72 (1H, d, J=1.8 Hz), 5.80 (1H, d, J=1.8 Hz), 6.62 (2H, s), 7.4–7.6 (4H, m).

REFERENCE EXAMPLE 26

6-Amino-4-(3-bromophenyl)-1-propyl-2 (1H)-pyridone
Starting compounds: ethyl 3-(3-bromophenyl)-4-cyano-3-butenoate and propylamine
Mass spectrometry data (m/z): 306, 308 (M$^+$)
Nuclear magnetic resonance spectrum (DMSO-d$_6$, TMS internal standard) δ: 0.91 (3H, t, J=7.3 Hz), 1.5–1.6 (2H, m), 3.88 (2H, t, J=7.9 Hz), 5.65 (1H, d, J=1.8 Hz), 5.74 (1H, d, J=1.8 Hz), 6.60 (2H, s), 7.3–7.7 (4H, m).

REFERENCE EXAMPLE 27

6-Amino-4-(3-chlorophenyl)-1-cyclopropyl-2(1H)-pyridone
Starting compounds: ethyl 3-(3-chlorophenyl)-4-cyano-3-butenoate and cyclopropylamine
Mass spectrometry data (m/z): 260 (M$^+$)
Nuclear magnetic resonance spectrum (DMSO-d$_6$, TMS internal standard) δ: 0.67–0.76 (2H, m), 1.16–1.21 (2H, m), 2.53–2.57 (1H, m), 5.61 (1H, d, J=1.8 Hz), 5.68 (1H, d, J=1.8 Hz), 6.59 (2H, s), 7.46–7.54 (4H, m).

The following compound of Reference Example 28 was obtained in the same manner as described in Reference Example 1

REFERENCE EXAMPLE 28

N-[3-(3-Bromobenzoyl)-2-pyridyl]-N-ethylacetamide
Starting compound: 3-(3-bromobenzoyl)-2-ethylaminopyridine
Mass spectrometry data (m/z): 346, 348 (M$^+$)
Nuclear magnetic resonance spectrum (CDCl$_3$, TMS internal standard) δ: 1.07, 1.39 (3H, br×2), 1.89, 2.09 (3H, br×2), 3.50, 4.03 (2H, br×2), 7.10–8.05 (6H, m), 8.59, 8.73 (1H, br×2).

The following compound of Reference Example 29 was obtained in the same manner as described in Reference Example 23.

REFERENCE EXAMPLE 29

6-Amino-1-ethyl-4-phenyl-2(1H)-pyridone
Starting compounds: ethyl 4-cyano-3-phenyl-3-butenoate and ethylamine
Mass spectrometry data (m/z): 214 (M$^+$)
Nuclear magnetic resonance spectrum (DMSO-d$_6$, TMS internal standard) δ: 1.15 (3H, t, J=7.0 Hz), 4.00 (2H, q, J=7.0 Hz), 5.68 (1H, d, J=2.1 Hz), 5.74 (1H, d, J=2.1 Hz), 6.58 (2H, s), 7.35–7.60 (5H, m).

REFERENCE EXAMPLE 30

An acetic anhydride solution (20 ml) of 1.5 g of 3-cyclohexylcarbonyl-2-ethylaminopyridine was heated under reflux for 4 hours. The reaction solution was concentrated under reduced pressure, and the resulting residue was purified by silica gel column chromatography (toluene-ethyl acetate) to give 1.1 g of N-(3-cyclohexylcarbonyl-2-pyridyl)-N-ethylacetamide.

Mass spectrometry data (m/z): FAB-MS 275 (M$^+$+1)

Nuclear magnetic resonance spectrum (CDCl$_3$, TMS internal standard) δ: 1.10–1.50 (8H, m), 1.65–2.00 (8H, m), 2.22 (1H, br), 2.94 (1H, br), 3.40–4.15 (2H, br), 7.39 (1H, br), 7.90 (1H, dd, J=7.3 Hz, 1.8 Hz), 8.64 (1H, br)

The following compounds of reference Examples 31 and 32 were obtained in the same manner as described in Reference Example 30.

REFERENCE EXAMPLE 31

N-(3-Cyclopentylcarbonyl-2-pyridyl)-N-ethylacetamide
Starting compound: 3-cyclopentylcarbonyl-2-ethylaminopyridine Mass spectrometry data (m/z): FAB-MS 261 (M$^+$+1)

Nuclear magnetic resonance spectrum (CDCl$_3$, TMS internal standard) δ: 1.12, 1.31 (3H, br×2), 1.55–2.25 (11H, m), 3.43 (1H, m), 3.50–4.10 (2H, m), 7.28, 7.39 (1H, br×2), 7.93 (1H, m), 8.52, 8.63 (1H, br×2)

REFERENCE EXAMPLE 32

N-[3-(1-Adamantylcarbonyl)-2-pyridyl]-N-ethylacetamide
Starting compound: 3-(1-adamantylcarbonyl)-2-ethylaminopyridine Mass spectrometry data (m/z): FAB-MS 327 (M$^+$+1)

Nuclear magnetic resonance spectrum (CDCl$_3$, TMS internal standard) δ: 1.15, 1.26 (3H, br×2), 1.64–2.05 (15H, m), 3.66, 3.84 (2H, br×2), 7.32 (1H, br), 7.61 (1H, br), 8.56 (1H, br)

REFERENCE EXAMPLE 33

Ethyl 3-cyclohexyl-4-cyano-3-butenoate (8.2 g) and 15 ml of 28% ethylamine-methanol solution were added to a methanol solution (40 ml) of 1.0 g of sodium, and the mixture was allowed to stand overnight at room temperature. The reaction solution was poured into ice water and extracted with ethyl acetate. The ethyl acetate layer was dried over anhydrous magnesium sulfate, magnesium sulfate was removed by filtration and then the resulting filtrate was concentrated under reduced pressure. Thereafter, the resulting residue was washed with diethyl ether-diisopropyl ether to give 5.4 g of 6-amino-4-cyclohexyl-1-ethyl-2(1H)-pyridone.

Mass spectrometry data (m/z): FAB-MS 221 (M$^+$+1)

Nuclear magnetic resonance spectrum (CDCl$_3$, TMS internal standard) δ: 1.15–1.40 (8H, m), 1.70–1.85 (5H, m), 2.18 (1H, m), 4.08 (2H, q, J=7.3 Hz), 4.25 (2H, s), 5.38 (1H, d, J=1.8 Hz), 5.86 (1H, d, J=1.8 Hz)

REFERENCE EXAMPLE 34

In an atmosphere of argon, 1.69M n-butyl lithiumhexane solution (53 ml, 90.0 mmol) was added dropwise to an ether solution (150 ml) of diisopropylamine (9.61 g, 95.0 mmol) which was cooled at −78° C. After 15 minutes of stirring, an ether solution (20 ml) of tert-butyl acetate (10.5 g, 90.5 mmol) was slowly added dropwise. After 30 minutes of stirring, a tetrahydrofuran solution (30 ml) of 3-benzoyl-2-pivaloylaminopyridine (12.0 g, 42.6 mmol) was added dropwise. After 30 minutes of stirring, this was warmed up to room temperature and stirred for 5 hours. The reaction solution was poured into water and extracted with chloroform. The organic layer was dried over anhydrous magnesium sulfate. After removing magnesium sulfate by filtration, the resulting filtrate was concentrated under reduced pressure to give tert-butyl 2-pivaloylamino-β-hydroxy-β-phenyl-3-pyridinepropanoate (16.9 g, 100%).

Mass spectrometry data (m/z): FAB-MS 399 (M$^+$+1)

Nuclear magnetic resonance spectrum (CDCl$_3$, TMS internal standard) δ: 1.02 (9H, s), 2.91 (1H, d, J=16.6 Hz), 6.19 (1H, s), 7.03 (1H, dd, J=7.8, 4.9 Hz), 7.23–7.56 (5H, m), 7.55 (1H, dd, J=7.8, 1.5 Hz), 8.51–8.52 (1H, m), 9.68 (1H, br)

REFERENCE EXAMPLE 35

Tert-butyl 2-pivaloylamino-β-hydroxy-β-phenyl-3-pyridinepropanoate (2.09 g, 5.25 mmol) was dissolved in a mixed solvent of 3N hydrochloric acid aqueous solution (10 ml) and dioxane (10 ml), and the solution was heated under reflux for 3 days. After cooling to room temperature, saturated sodium bicarbonate aqueous solution was added for neutralization. The reaction mixture was filtered, and the resulting crystals were thoroughly washed with water and recrystallized from acetonitrile to give 4-phenyl-1,8-naphthyridin-2(1H)-one (600 mg, 51%).

Sublimation at 200° C. or more CH$_3$CN

Elemental analysis data (for C$_{14}$H$_{10}$N$_2$O)

|  | C (%) | H (%) | N (%) |
|---|---|---|---|
| Calcd. | 75.66 | 4.54 | 12.60 |
| Found | 75.68 | 4.65 | 12.70 |

Chemical structures of the compounds obtained in Reference Examples 1 to 33 are shown in the following table.

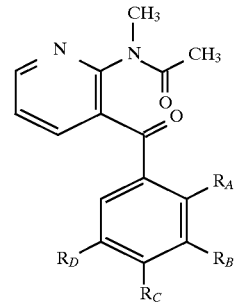

| Reference Example No | R$_A$ | R$_B$ | R$_C$ | R$_D$ |
|---|---|---|---|---|
| 1 | H | Cl | H | H |
| 2 | H | H | H | H |
| 3 | H | —CH$_3$ | H | H |
| 4 | —CH$_3$ | H | H | H |
| 5 | H | —OCH$_3$ | H | H |
| 6 | H | H | Cl | H |
| 7 | H | Br | H | H |
| 8 | Cl | Cl | H | H |
| 9 | H | Cl | H | Cl |
| 10 | H | —CF$_3$ | H | H |
| 11 | H | —CN | H | H |
| 12 | H | —NO$_2$ | H | H |

-continued

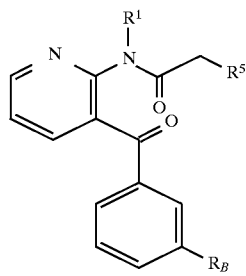

| Reference Example No. | R¹ | R⁵ | R_B |
|---|---|---|---|
| 13 | —CH₃ | —CH₃ | H |
| 14 | —CH₂CH₃ | H | H |
| 15 | —CH₂CH₃ | H | Cl |
| 16 | —CH₂CH₂CH₃ | H | H |
| 17 | —CH(CH₃)₂ | H | H |
| 18 | cyclopropyl | H | H |
| 19 | cyclobutyl | H | H |
| 20 | phenyl | H | H |
| 21 | —(CH₂)₄-phenyl | H | —NO₂ |
| 22 | —CH₂-(2-pyridyl) | H | H |
| 28 | —CH₂CH₃ | H | Br |

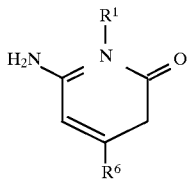

| Reference Example No. | R¹ | R⁶ |
|---|---|---|
| 23 | —CH₂CH₃ | 3-Br-phenyl |

-continued

| | R¹ | R⁵ | (aryl/cycloalkyl) |
|---|---|---|---|
| 24 | —CH₂CH₃ | | 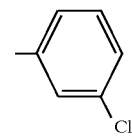 3-Cl-phenyl |
| 25 | —CH₃ | | 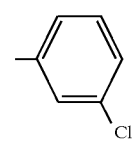 3-Cl-phenyl |
| 26 | —CH₂CH₂CH₃ | | 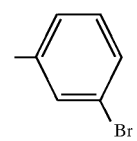 3-Br-phenyl |
| 27 |  cyclopropyl | | 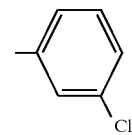 3-Cl-phenyl |
| 29 | —CH₂CH₃ | | 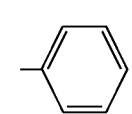 phenyl |
| 33 | —CH₂CH₃ | | 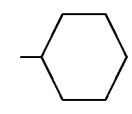 cyclohexyl |

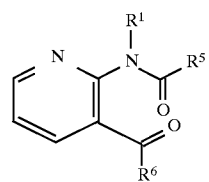

| Reference Example No. | R¹ | R⁵ | R⁶ |
|---|---|---|---|
| 30 | —CH₂CH₃ | —CH₃ | cyclohexyl |
| 31 | —CH₂CH₃ | —CH₃ | cyclopentyl |
| 32 | —CH₂CH₃ | —CH₃ | adamantyl |

Example 1

Under ice-cooling, potassium tert-butoxide (623 mg, 5 mmol) was added to tetrahydrofuran (10 ml) solution of N-[3-(3-chlorobenzoyl)-2-pyridyl]-N-methylacetamide (1.40 g, 5 mmol), and the mixture was stirred at room temperature for 30 minutes. The reaction solution was mixed with water and extracted with ethyl acetate, and the organic layer was dried over anhydrous magnesium sulfate. After removing magnesium sulfate by filtration, the filtrate was concentrated under reduced pressure and the resulting residue was purified by silica gel column chromatography (benzene-ethyl acetate) to give 4-(3-chlorophenyl)-1-methyl-1,8-naphthyridin-2(1H)-one (709 mg, 54%).

Melting point 168°–170° C. (AcOEt-iPr$_2$O)

Elemental analysis data (for C$_{15}$H$_{11}$N$_2$OCl)

|  | C (%) | H (%) | N (%) | Cl (%) |
|---|---|---|---|---|
| Calcd. | 66.55 | 4.10 | 10.35 | 13.10 |
| Found | 66.60 | 4.03 | 10.37 | 13.12 |

The following compounds of Examples 2 to 22 were obtained in the same manner as described in Example 1.

Example 2

1-Methyl-4-phenyl-1,8-naphthyridin-2(1H)-one

Starting compound: N-methyl-N-(3-benzoyl-2-pyridyl)acetamide

Melting point 133°–135° C. (iPr$_2$O)

Elemental analysis data (for C$_{15}$H$_{12}$N$_2$O)

|  | C (%) | H (%) | N (%) |
|---|---|---|---|
| Calcd. | 76.25 | 5.12 | 11.86 |
| Found | 76.26 | 5.23 | 11.85 |

Example 3

1-Methyl-4-(3-methylphenyl)-1,8-naphthyridin-2(1H)-one

Starting compound: N-methyl-N-[3-(3-benzoyl)-2-pyridyl]acetamide

Melting point 141°–143° C. (AcOEt-iPr$_2$O)

Elemental analysis data (for C$_{16}$H$_{14}$N$_2$O)

|  | C (%) | H (%) | N (%) |
|---|---|---|---|
| Calcd. | 76.78 | 5.64 | 11.19 |
| Found | 76.95 | 5.65 | 11.20 |

Example 4

1-Methyl-4-(2-methylphenyl)-1,8-naphthyridin-2(1H)-one

Starting compound: N-methyl-N-[3-(2-methylbenzoyl)-2-pyridyl]acetamide

Melting point 128°–129° C. (iPr$_2$O)

Elemental analysis data (for C$_{16}$H$_{14}$N$_2$O)

|  | C (%) | H (%) | N (%) |
|---|---|---|---|
| Calcd. | 76.78 | 5.64 | 11.19 |
| Found | 76.75 | 5.59 | 11.18 |

Example 5

4-(3-Methoxyphenyl)-1-methyl-1,8-naphthyridin-2(1H)-one

Starting compound: N-[3-(3-methoxybenzoyl)-2-pyridyl]-N-methylacetamide

Melting point 157°–158° C. (AcOEt-iPr$_2$O)

Elemental analysis data (for C$_{16}$H$_{14}$N$_2$O$_2$)

|  | C (%) | H (%) | N (%) |
|---|---|---|---|
| Calcd. | 72.17 | 5.30 | 10.52 |
| Found | 72.03 | 5.32 | 10.46 |

Example 6

4-(4-Chlorophenyl)-1-methyl-1,8-naphthyridin-2(1H)-one

Starting compound: N-[3-(4-chlorobenzoyl)-2-pyridyl]-N-methylacetamide

Melting point 149°–150° C. (AcOEt-iPr$_2$O)

Elemental analysis data (for C$_{15}$H$_{11}$N$_2$OCl)

|  | C (%) | H (%) | N (%) | Cl (%) |
|---|---|---|---|---|
| Calcd. | 66.55 | 4.10 | 10.35 | 13.10 |
| Found | 66.59 | 4.02 | 10.33 | 12.98 |

Example 7

4-(3-Bromophenyl)-1-methyl-1,8-naphthyridin-2(1H)-one

Starting compound: N-[3-(3-bromobenzoyl)-2-pyridyl]-N-methylacetamide

Melting point 158°–159° C. (AcOEt)

Elemental analysis data (for C$_{15}$H$_{11}$N$_2$OBr)

|  | C (%) | H (%) | N (%) | Br (%) |
|---|---|---|---|---|
| Calcd. | 57.16 | 3.52 | 8.89 | 25.35 |
| Found | 57.18 | 3.54 | 8.94 | 25.18 |

Example 8

4-(2,3-Dichlorophenyl)-1-methyl-1,8-naphthyridin-2(1H)-one

Starting compound: N-[3-(2,3-dichlorobenzoyl)-2-pyridyl]-N-methylacetamide

Melting point 192°–193° C. (AcOEt-iPr$_2$O)

Elemental analysis data (for $C_{15}H_{10}N_2OCl_2$)

|  | C (%) | H (%) | N (%) | Cl (%) |
|---|---|---|---|---|
| Calcd. | 59.04 | 3.30 | 9.18 | 23.24 |
| Found | 58.94 | 3.20 | 9.24 | 22.97 |

Example 9

4-(3,5-Dichlorophenyl)-1-methyl-1,8-naphthyridin-2(1H)-one
Starting compound: N-[3-(3,5-dichlorobenzoyl)-2-pyridyl]-N-methylacetamide
  Melting point 227°–228° C. (AcOEt)
  Elemental analysis data (for $C_{15}H_{10}N_2OCl_2$)

|  | C (%) | H (%) | N (%) | Cl (%) |
|---|---|---|---|---|
| Calcd. | 59.04 | 3.30 | 9.18 | 23.24 |
| Found | 59.07 | 3.19 | 9.18 | 23.16 |

Example 10

4-(3-Trifluoromethylphenyl)-1-methyl-1,8-naphthyridin-2(1H)-one
Starting compound: N-[3-(3-trifluorobenzoyl)-2-pyridyl]-N-methylacetamide
  Melting point 166°–168° C. (AcOEt-iPr$_2$O)
  Elemental analysis data (for $C_{16}H_{11}N_2OF_3$)

|  | C (%) | H (%) | N (%) | F (%) |
|---|---|---|---|---|
| Calcd. | 63.16 | 3.64 | 9.21 | 18.73 |
| Found | 63.18 | 3.64 | 9.21 | 18.63 |

Example 11

4-(3-Cyanophenyl)-1-methyl-1,8-naphthyridin-2(1H)-one
Starting compound: N-[3-(3-cyanobenzoyl)-2-pyridyl)-N-methylacetamide
  Melting point 260°–262° C. (CHCl$_3$-AcOEt)
  Elemental analysis data (for $C_{16}H_{11}N_3O$)

|  | C (%) | H (%) | N (%) |
|---|---|---|---|
| Calcd. | 73.55 | 4.24 | 16.08 |
| Found | 73.59 | 4.27 | 16.07 |

Example 12

1-Methyl-4-(3-nitrophenyl)-1,8-naphthyridin-2(1H)-one
Starting compound: N-methyl-N-[3-(3-nitrobenzoyl)-2-pyridyl]acetamide
  Melting point 233°–234° C. (AcOEt)

Elemental analysis data (for $C_{15}H_{11}N_3O_3$)

|  | C (%) | H (%) | N (%) |
|---|---|---|---|
| Calcd. | 64.05 | 3.94 | 14.94 |
| Found | 63.78 | 3.83 | 14.89 |

Example 13

1,3-Dimethyl-4-phenyl-1,8-naphthyridin-2(1H)-one
Starting compound: N-(3-benzoyl-2-pyridyl)-N-methylpropionamide
  Melting point 145°–147° C. (iPr$_2$O)
  Elemental analysis data (for $C_{16}H_{14}N_2O$)

|  | C (%) | H (%) | N (%) |
|---|---|---|---|
| Calcd. | 76.78 | 5.64 | 11.19 |
| Found | 76.91 | 5.65 | 11.24 |

Example 14

1-Ethyl-4-phenyl-1,8-naphthyridin-2(1H)-one
Starting compound: N-(3-benzoyl-2-pyridyl)-N-ethylacetamide
  Melting point 100°–101° C. (iPr$_2$O)
  Elemental analysis data (for $C_{16}H_{14}N_2O$)

|  | C (%) | H (%) | N (%) |
|---|---|---|---|
| Calcd. | 76.78 | 5.64 | 11.19 |
| Found | 76.74 | 5.64 | 11.15 |

Example 15

4-(3-Chlorophenyl)-1-ethyl-1,8-naphthyridin-2(1H)-one
Starting compound: N-[3-(3-chlorobenzoyl)-2-pyridyl]-N-ethylacetamide
  Melting point 99°–100° C. (iPr$_2$O-hexane)
  Elemental analysis data (for $C_{16}H_{13}N_2OCl$)

|  | C (%) | H (%) | N (%) | Cl (%) |
|---|---|---|---|---|
| Calcd. | 67.49 | 4.60 | 9.84 | 12.45 |
| Found | 67.41 | 4.55 | 9.87 | 12.60 |

Example 16

4-Phenyl-1-propyl-1,8-naphthyridin-2(1H)-one
Starting compound: N-(3-benzoyl-2-pyridyl)-N-propylacetamide
  Melting point 99.0°–99.5° C. (iPr$_2$O)
  Elemental analysis data (for $C_{17}H_{16}N_2O$)

|  | C (%) | H (%) | N (%) |
|---|---|---|---|
| Calcd. | 77.25 | 6.10 | 10.60 |
| Found | 77.32 | 6.15 | 10.60 |

Example 17

1-Isopropyl-4-phenyl-1,8-naphthyridin-2(1H)-one
Starting compound: N-(3-benzoyl-2-pyridyl)-N-isopropylacetamide Melting point 110.5°–111.0° C. (iPr$_2$O-hexane)
Elemental analysis data (for C$_{17}$H$_{16}$N$_2$O)

|  | C (%) | H (%) | N (%) |
|---|---|---|---|
| Calcd. | 77.25 | 6.10 | 10.60 |
| Found | 77.32 | 6.14 | 10.62 |

Example 18

1-Cyclopropyl-4-phenyl-1,8-naphthyridin-2(1H)-one
Starting compound: N-(3-benzoyl-2-pyridyl)-N-cyclopropylacetamide
  Melting point 128°–129° C. (iPr$_2$O-AcOEt)
  Elemental analysis data (for C$_{17}$H$_{14}$N$_2$O)

|  | C (%) | H (%) | N (%) |
|---|---|---|---|
| Calcd. | 77.84 | 5.38 | 10.68 |
| Found | 77.82 | 5.44 | 10.70 |

Example 19

1-Cyclobutyl-4-phenyl-1,8-naphthyridin-2(1H)-one
Starting compound: N-(3-benzoyl-2-pyridyl]-N-cyclobutylacetamide
  Melting point 136°–138° C. (AcOEt)
  Elemental analysis data (for C$_{18}$H$_{16}$N$_2$O)

|  | C (%) | H (%) | N (%) |
|---|---|---|---|
| Calcd. | 78.24 | 5.84 | 10.14 |
| Found | 78.15 | 5.88 | 10.11 |

Example 20

1,4-Diphenyl-1,8-naphthyridin-2(1H)-one
Starting compound: N-(3-benzoyl-2-pyridyl)-N-phenylacetamide
  Melting point 210°–212° C. (AcOEt)
  Elemental analysis data (for C$_{20}$H$_{14}$N$_2$O)

|  | C (%) | H (%) | N (%) |
|---|---|---|---|
| Calcd. | 80.52 | 4.73 | 9.39 |
| Found | 80.57 | 4.68 | 9.31 |

Example 21

4-(3-Nitrophenyl)-1-(4-phenylbutyl)-1,8-naphthyridin-2(1H)-one
Starting compound: N-[3-(3-nitrobenzoyl)-2-pyridyl]-N-(4-phenylbutyl)acetamide
  Melting point 86°–88° C. (Et$_2$O-iPr$_2$O)
  Elemental analysis data (for C$_{24}$H$_{21}$N$_3$O$_3$)

|  | C (%) | H (%) | N (%) |
|---|---|---|---|
| Calcd. | 72.17 | 5.30 | 10.52 |
| Found | 71.89 | 5.26 | 10.41 |

Example 22

4-Phenyl-1-(2-pyridylmethyl)-1,8-naphthyridin-2(1H)-one

Starting compound: N-(3-benzoyl-2-pyridyl)-N-(2-pyridylmethyl)acetamide
  Melting point 110°–112° C. (iPr$_2$O)
  Elemental analysis data (for C$_{20}$H$_{15}$N$_3$O)

|  | C (%) | H (%) | N (%) |
|---|---|---|---|
| Calcd. | 76.66 | 4.82 | 13.41 |
| Found | 76.88 | 4.88 | 13.33 |

Example 23

Zinc (4.4 g, 67 mmol) was added to a mixture of 1-methyl-4-(3-nitrophenyl)-1,8-naphthyridin-2(1H)-one (0.95 g, 3.4 mmol) obtained in Example 12, methanol (20 ml) and an aqueous solution (20 ml) of ammonium chloride (3.6 g, 67 mmol) under ice-cooling, and the mixture was stirred for 4 hours under ice-cooling and then for 3 hours at room temperature. After removing insoluble matter by filtration, the filtrate was concentrated under reduced pressure, water was added to the resulting residue, followed by extraction with chloroform. The organic layer was dried over anhydrous magnesium sulfate, magnesium sulfate was removed by filtration and then the resulting filtrate was concentrated under reduced pressure. Thereafter, the resulting residue was purified by silica gel column chromatography (toluene-ethyl acetate) to give 4-(3-aminophenyl)-1-methyl-1,8-naphthyridin-2(1H)one (693 mg, 82%).

Melting point 154°–156° C. (AcOEt)
Elemental analysis data (for C$_{15}$H$_{13}$N$_3$O)

|  | C (%) | H (%) | N (%) |
|---|---|---|---|
| Calcd. | 71.70 | 5.21 | 16.72 |
| Found | 71.80 | 5.26 | 16.61 |

Example 24

A mixture of diphosphorus pentoxide (10.5 g) and phosphoric acid (5 ml) was stirred at 140° C. until it became transparent. Then, 6-amino-4-(3-chlorophenyl)-1-methyl-2(1H)-pyridone (2.34 g, 10 mmol) and acetylacetone (1.05 ml, 10 mmol) were added to this solution, and the mixture was stirred at 140° C. for 3 hours. The reaction solution was poured into ice water, made alkaline by adding 1N sodium hydroxide aqueous solution and then extracted with ethyl acetate. After drying the organic layer with anhydrous magnesium sulfate, magnesium sulfate was removed by filtration and the filtrate was concentrated under reduced pressure. The residue was then purified by silica gel column chromatography (benzene-ethyl acetate) to give 4-(3-chlorophenyl)-1,5,7-trimethyl-1,8-naphthyridin-2(1H)-one (2.11 g, 71%).

Melting point 161°–162° C. (AcOEt-iPr$_2$O)
Elemental analysis data (for C$_{17}$H$_{15}$N$_2$OCl)

|  | C (%) | H (%) | N (%) | Cl (%) |
|---|---|---|---|---|
| Calcd. | 68.34 | 5.06 | 9.38 | 11.87 |
| Found | 68.34 | 5.01 | 9.46 | 11.75 |

The following compounds of Examples 25 to 30 and 32 to 35 were obtained in the same manner as described in Example 24.

Example 25

1,5,6,7-Tetramethyl-4-phenyl-1,8-naphthyridin-2(1H)-one

Starting compounds: 6-amino-1-methyl-4-phenyl-2(1H)-pyridone and 3-methyl-2,4-pentanedione Melting point 151°–153° C. (AcOEt-iPr$_2$O)

Elemental analysis data (for $C_{18}H_{18}N_2O$)

|  | C (%) | H (%) | N (%) |
|---|---|---|---|
| Calcd. | 77.67 | 6.52 | 10.06 |
| Found | 77.55 | 6.53 | 9.99 |

Example 26

7-Ethyl-1,5-dimethyl-4-phenyl-1,8-naphthyridin-2(1H)-one

Starting compounds: 6-amino-1-methyl-4-phenyl-2(1H)-pyridone and 2,4-hexanedion

Melting point 88°–88.5° C. (iPr$_2$O-hexane)

Elemental analysis data (for $C_{18}H_{18}N_2O$)

|  | C (%) | H (%) | N (%) |
|---|---|---|---|
| Calcd. | 77.67 | 6.52 | 10.06 |
| Found | 77.67 | 6.54 | 10.05 |

Example 27

4-(3-Chlorophenyl)-7-ethyl-1,5-dimethyl-1,8-naphthyridin-2(1H)-one

Starting compounds: 6-amino-4-(3-chlorophenyl)-1-methyl-2(1H)-pyridone and 2,4-hexanedione Melting point 111°–112.5° C. (iPr$_2$O)

Elemental analysis data (for $C_{18}H_{17}N_2OCl$)

|  | C (%) | H (%) | N (%) | Cl (%) |
|---|---|---|---|---|
| Calcd. | 69.12 | 5.48 | 8.96 | 11.33 |
| Found | 69.27 | 5.47 | 9.09 | 11.44 |

Example 28

5,7-Diethyl-1-methyl-4-phenyl-1,8-naphthyridin-2(1H)-one

Starting compounds: 6-amino-1-methyl-4-phenyl-2(1H)-pyridone and 3,5-heptanedione Melting point 68°–69° C. (iPr$_2$O-hexane)

Elemental analysis data (for $C_{19}H_{20}N_2O$)

|  | C (%) | H (%) | N (%) |
|---|---|---|---|
| Calcd. | 78.05 | 6.89 | 9.58 |
| Found | 78.17 | 6.98 | 9.62 |

Example 29

4-(3-Chlorophenyl)-1-ethyl-5,7-dimethyl-1,8-naphthyridin-2(1H)-one

Starting compounds: 6-amino-4-(3-chlorophenyl)-1-ethyl-2(1H)-pyridone and acetylacetone Melting point 93°–94° C. (iPr$_2$O)

Elemental analysis data (for $C_{18}H_{17}N_2OCl$)

|  | C (%) | H (%) | N (%) | Cl (%) |
|---|---|---|---|---|
| Calcd. | 69.12 | 5.48 | 8.96 | 11.33 |
| Found | 68.99 | 5.38 | 8.89 | 11.13 |

Example 30

4-(3-Bromophenyl)-1-ethyl-5,7-dimethyl-1,8-naphthyridin-2(1H)-one

Starting compounds: 6-amino-4-(3-bromophenyl)-1-ethyl-2(1H)-pyridone and acetylacetone Melting point 135°–137° C. (iPr$_2$O)

Elemental analysis data (for $C_{18}H_{17}N_2OBr$)

|  | C (%) | H (%) | N (%) | Br (%) |
|---|---|---|---|---|
| Calcd. | 60.52 | 4.80 | 7.84 | 22.37 |
| Found | 60.58 | 4.77 | 7.83 | 22.18 |

Example 31

A mixture of diphosphorus pentoxide (10.4 g) and phosphoric acid (5 ml) was stirred at 140° C. until it became transparent. Then, 6-amino-4-(3-bromophenyl)-1-ethyl-2(1H)-pyridone (2.5 g, 8.5 mmol) and 2,4-hexanedione (1.1 ml) were added to this solution, and the mixture was stirred at 140° C. for 3 hours. The reaction solution was poured into ice water, made alkaline by adding 1N sodium hydroxide aqueous solution and then extracted with ethyl acetate. After drying the organic layer with anhydrous magnesium sulfate, magnesium sulfate was removed by filtration and the filtrate was concentrated under reduced pressure. The resulting residue was then purified by silica gel column chromatography (benzene-ethyl acetate) to give 4-(3-bromophenyl)-1,7-diethyl-5-methyl-1,8-naphthyridin-2(1H)-one (2.3 g, 73%).

Melting point 107°–108.5° C. (iPr$_2$O)

Elemental analysis data (for $C_{19}H_{19}N_2OBr$)

|  | C (%) | H (%) | N (%) | Br (%) |
|---|---|---|---|---|
| Calcd. | 61.47 | 5.16 | 7.55 | 21.52 |
| Found | 61.40 | 5.14 | 7.49 | 21.74 |

Example 32

4-(3-Bromophenyl)-5,7-dimethyl-1-propyl-1,8-naphthyridin-2(1H)-one

Starting compounds: 6-amino-4-(3-bromophenyl)-1-propyl-2(1H)-pyridone and acetylacetone Melting point 121°–122° C. (iPr$_2$O-hexane)
Elemental analysis data (for C$_{19}$H$_{19}$N$_2$OBr)

|  | C (%) | H (%) | N (%) | Br (%) |
|---|---|---|---|---|
| Calcd. | 61.47 | 5.16 | 7.55 | 21.52 |
| Found | 61.54 | 5.09 | 7.52 | 21.27 |

Example 33

4-(3-Bromophenyl)-7-ethyl-5-methyl-1-propyl-1,8-naphthyridin-2(1H)-one
Starting compounds: 6-amino-4-(3-bromophenyl)-1-propyl-2(1H)-pyridone and 2,4-hexanedione
Melting point 107°–108° C. (iPr$_2$O-hexane)
Elemental analysis data (for C$_{20}$H$_{21}$N$_2$OBr)

|  | C (%) | H (%) | N (%) | Br (%) |
|---|---|---|---|---|
| Calcd. | 62.35 | 5.49 | 7.27 | 20.74 |
| Found | 62.35 | 5.48 | 7.28 | 20.61 |

Example 34

4-(3-Chlorophenyl)-1-cyclopropyl-5,7-dimethyl-1,8-naphthyridin-2(1H)-one
Starting compounds: 6-amino-4-(3-chlorophenyl)-1-cyclopropyl-2(1H)-pyridone and acetylacetone
Melting point 110°–112° C. (Ipr$_2$O)
Elemental analysis data (for C$_{19}$H$_{17}$N$_2$OCl)

|  | C (%) | H (%) | N (%) | Cl (%) |
|---|---|---|---|---|
| Calcd. | 70.26 | 5.28 | 8.62 | 10.91 |
| Found | 70.25 | 5.20 | 8.58 | 10.86 |

Example 35

4-(3-Chlorophenyl)-1-cyclopropyl-7-ethyl-5-methyl-1,8-naphthyridin-2(1H)-one
Starting compounds: 6-amino-4-(3-chlorophenyl)-1-cyclopropyl-2(1H)-pyridone and 2,4-hexanedione
Melting point 126°–128° C. (hexane)
Elemental analysis data (for C$_{20}$H$_{19}$N$_2$OCl)

|  | C (%) | H (%) | N (%) | Cl (%) |
|---|---|---|---|---|
| Calcd. | 70.90 | 5.65 | 8.27 | 10.46 |
| Found | 70.86 | 5.63 | 8.26 | 10.43 |

Example 36

A 1 M-dichloromethane solution of boron tribromide (25 ml, 25 mmol) was added to a dichloromethane solution (30 ml) of 4-(3-methoxyphenyl)-1-methyl-1,8-naphthyridin-2(1H)-one (1.3 g, 4.9 mmol) at −35° C., and the mixture was gradually warmed up to room temperature and then stirred at room temperature for 2 hours. Methanol (10 ml) was added to the reaction solution at −60° C., and the mixture was warmed up to room temperature and then stirred at room temperature for 30 minutes. The reaction solution was concentrated under reduced pressure, methanol (30 ml) was added to the residue, and the mixture was concentrated under reduced pressure. The residue was purified by silica gel column chromatography (benzene-ethyl acetate) to give 4-(3-hydroxyphenyl)-1-methyl-1,8-naphthyridin-2(1H)-one (0.29 g, 23%).
Melting point 260°–261° C. (MeOH)
Elemental analysis data (for C$_{15}$H$_{12}$N$_2$O$_2$)

|  | C (%) | H (%) | N (%) |
|---|---|---|---|
| Calcd. | 71.42 | 4.79 | 11.10 |
| Found | 71.34 | 4.85 | 11.16 |

The following compound of Example 37 was obtained in the same manner as described in Example 1.

Example 37

4-(3-Bromophenyl)-1-ethyl-1,8-naphthyridin-2(1H)-one
Starting compound: N-[3-(3-bromobenzoyl)-2-pyridyl]-N-ethylacetamide
Melting point 104°–106° C. (iPr$_2$O)
Elemental analysis data (for C$_{16}$H$_{13}$N$_2$OBr)

|  | C (%) | H (%) | N (%) | Br (%) |
|---|---|---|---|---|
| Calcd. | 58.38 | 3.98 | 8.51 | 24.27 |
| Found | 58.33 | 3.85 | 8.46 | 24.32 |

The following compounds of Examples 38 to 40 were obtained in the same manner as described in Example 31.

Example 38

1-Ethyl-5,7-dimethyl-4-phenyl-1,8-naphthyridin-2(1H)-one
Starting compounds: 6-amino-1-ethyl-4-phenyl-2(1H)-pyridone and 2,4-pentanedione
Melting point 113°–114° C. (iPr$_2$O-hexane)
Elemental analysis data (for C$_{18}$H$_{18}$N$_2$O)

|  | C (%) | H (%) | N (%) |
|---|---|---|---|
| Calcd. | 77.67 | 6.52 | 10.06 |
| Found | 77.93 | 6.54 | 9.93 |

Example 39

4-(3-Chlorophenyl)-1,7-diethyl-5-methyl-1,8-naphthyridin-2(1H)-one
Starting compound: 6-amino-4-(3-chlorophenyl)-1-ethyl-2(1H)-pyridone
Melting point 88°–90° C. (hexane)
Elemental analysis data (for C$_{17}$H$_{19}$N$_2$OCl)

|  | C (%) | H (%) | N (%) | Cl (%) |
|---|---|---|---|---|
| Calcd. | 69.83 | 5.86 | 8.57 | 10.85 |
| Found | 69.44 | 5.85 | 8.46 | 11.09 |

Example 40

1,7-Diethyl-5-methyl-4-phenyl-1,8-naphthyridin-2(1H)-one
Starting compounds: 6-amino-1-ethyl-4-phenyl-2(1H)-pyridone and 2,4-hexanedione Melting point 97°–98° C. (iPr$_2$O-hexane)

Elemental analysis data (for C$_{19}$H$_{20}$N$_2$O)

|  | C (%) | H (%) | N (%) |
|---|---|---|---|
| Calcd. | 78.05 | 6.89 | 9.58 |
| Found | 78.02 | 6.88 | 9.45 |

Example 41

Sodium hydride (210 mg, 60% dispersion) was added to a dioxane solution (100 ml) of 4-phenyl-1,8-naphthyridin-2(1H)-one (1.01 g, 4.55 mmol), and the mixture was stirred at 110° C. for 30 minutes. After cooling to room temperature, propargyl bromide (650 mg, 5.46 mmol) and lithium bromide (830 mg, 9.55 mmol) were added, and the mixture was heated under reflux for 2 days. After cooling to room temperature, brine was added, and the mixture was extracted with chloroform. The organic layer was washed with brine and dried over anhydrous sodium sulfate. After removing sodium sulfate by filtration, the solvent was evaporated under reduced pressure and the resulting residue was purified by silica gel column chromatography (hexane-ethyl acetate) and further recrystallized from diisopropyl ether to give 4-phenyl-1-propargyl-1,8-naphthyridin-2(1H)-one (107 mg, 9%).

Melting point 127°–129° C. (iPr$_2$O)

Elemental analysis data (for C$_{17}$H$_{12}$N$_2$O)

|  | C (%) | H (%) | N (%) |
|---|---|---|---|
| Calcd. | 78.44 | 4.65 | 10.76 |
| Found | 78.66 | 4.60 | 10.78 |

The following compound of Example 42 was obtained in the same manner as described in Example 41.

Example 42

1-Cyanomethyl-4-phenyl-1,8-naphthyridin-2(1H)-one

Starting compound: 4-phenyl-1,8-naphthyridin-2(1H)-one

Melting point 148°–150° C. (AcOEt-iPr$_2$O)

Elemental analysis data (for C$_{16}$H$_{11}$N$_3$O)

|  | C (%) | H (%) | N (%) |
|---|---|---|---|
| Calcd. | 73.55 | 4.24 | 16.08 |
| Found | 73.61 | 4.26 | 16.09 |

Example 43

Diphosphorous pentasulfide (740 mg, 3.33 mmol) was added to a dichloromethane solution (20 ml) of 4-(3-chlorophenyl)-7-ethyl-1,5-dimethyl-1,8-naphthyridin-2(1H)-one (900 mg, 2.88 mmol), and the mixture was heated under reflux for 3 days. The reaction solution was cooled to room temperature, mixed with water and then extracted with chloroform. The organic layer was washed with brine and dried over anhydrous sodium sulfate. After removing sodium sulfate by filtration, the solvent was evaporated under reduced pressure and the resulting residue was purified by silica gel column chromatography (benzene) and further recrystallized from a hexane-diisopropyl ether mixed solvent to give 4-(3-chlorophenyl)-7-ethyl-1,5-dimethyl-1,8-naphthyridine-2(1H)-thione (368 mg, 39%).

Melting point 131°–133° C. (iPr$_2$O)

Elemental analysis data (for C$_{18}$H$_{17}$N$_2$SCl)

|  | C (%) | H (%) | N (%) | S (%) | Cl (%) |
|---|---|---|---|---|---|
| Calcd. | 65.74 | 5.21 | 8.52 | 9.75 | 10.78 |
| Found | 65.70 | 5.22 | 8.46 | 10.07 | 10.87 |

The following compound of Example 44 was obtained in the same manner as described in Example 43.

Example 44

1-Ethyl-5,7-dimethyl-4-phenyl-1,8-naphthyridine-2(1H)-thione

Starting compound: 1-ethyl-5,7-dimethyl-4-phenyl-1,8-naphthylidin-2(1H)-one

Melting point 148°–149° C. (hexane)

Elemental analysis data (for C$_{18}$H$_{18}$N$_2$S)

|  | C (%) | H (%) | N (%) | S (%) |
|---|---|---|---|---|
| Calcd. | 73.43 | 6.16 | 9.51 | 10.89 |
| Found | 73.52 | 6.16 | 9.46 | 11.16 |

Example 45

Under ice-cooling, 2.9 g of 90% potassium tert-butoxide was added to 70 ml of tetrahydrofuran solution containing 6.4 g of N-(3-cyclohexylcarbonyl-2-pyridyl)-N-ethylacetamide, and the mixture was stirred at room temperature for 30 minutes. The reaction solution was mixed with water and extracted with ethyl acetate, and the resulting organic layer was dried over anhydrous magnesium sulfate. After removing magnesium sulfate by filtration, the filtrate was concentrated under reduced pressure and the resulting residue was purified by silica gel column chromatography (toluene-ethyl acetate) to give 4.5 g of 4-cyclohexyl-1-ethyl-1,8-naphthyridin-2(1H)-one.

Melting point 88°–89° C. (hexane)

Elemental analysis data (for C$_{16}$H$_{20}$N$_2$O)

|  | C (%) | H (%) | N (%) |
|---|---|---|---|
| Calcd. | 74.97 | 7.86 | 10.93 |
| Found | 74.84 | 7.87 | 10.93 |

Example 46

A 4N hydrogen chloride-ethyl acetate solution (2 ml) was added to a methanol solution (10 ml) of 4-cyclohexyl-1-ethyl-1,8-naphthyridin-2(1H)-one (641 mg), and the mixture was concentrated under reduced pressure. The resulting residue was then made into powder using isopropanol-diisopropyl ether to give 4-cyclohexyl-1-ethyl-1,8-naphthyridin-2(1H)-one 0.45 hydrochloride 0.25 hydrate (100 mg).

Elemental analysis data (for C$_{16}$H$_{20}$N$_2$O·0.45HCl·0.25H$_2$O)

|  | C (%) | H (%) | N (%) | Cl (%) |
|---|---|---|---|---|
| Calcd. | 69.31 | 7.62 | 10.10 | 5.75 |
| Found | 69.05 | 7.71 | 10.20 | 5.55 |

Mass spectrometry analysis data (m/z): 256 (M$^+$)

The following compounds of Examples 47 and 48 were obtained in the same manner as described in Example 45.

Example 47

4-Cyclopentyl-1-ethyl-1,8-naphthyridin-2(1H)-one

Starting compound: N-(3-cyclopentylcarbonyl-2-pyridyl)-N-ethylacetamide

Melting point 54°–55° C. (iPr$_2$O-hexane)

Elemental analysis data (for $C_{15}H_{18}N_2O$)

|  | C (%) | H (%) | N (%) |
|---|---|---|---|
| Calcd. | 74.35 | 7.49 | 11.56 |
| Found | 74.33 | 7.54 | 11.54 |

Example 48

4-(1-Adamantyl)-1-ethyl-1,8-naphthyridin-2(1H)-one

Starting compound: N-[3-(1-adamantylcarbonyl)-2-pyridyl]-N-ethylacetamide

Melting point 173°–175° C. (iPr$_2$O-hexane)

Elemental analysis data (for $C_{20}H_{24}N_2O$)

|  | C (%) | H (%) | N (%) |
|---|---|---|---|
| Calcd. | 77.89 | 7.84 | 9.08 |
| Found | 78.11 | 7.95 | 9.04 |

Example 49

A mixture of 5.0 g of diphosphorus pentoxide and 2.5 ml of phosphoric acid was stirred at 140° C. until it became transparent. Then, 1.1 g of 6-amino-4-cyclohexyl-1-ethyl-2(1H)-pyridone and 0.6 ml of 2,4-hexanedione were added to this solution, and the mixture was stirred at 140° C. for 3 hours. The reaction solution was poured into ice water, made alkaline by adding 1 N sodium hydroxide aqueous solution and then extracted with ethyl acetate. After drying the ethyl acetate layer over anhydrous magnesium sulfate, magnesium sulfate was removed by filtration and the filtrate was concentrated under reduced pressure. The residue was then purified by silica gel column chromatography (toluene-ethyl acetate) to give 1.2 g of 4-cyclohexyl-1,7-diethyl-5-methyl-1,8-naphthyridin-2(1H)-one.

Melting point 79°–80° C. (hexane)

Elemental analysis data (for $C_{19}H_{26}N_2O$)

|  | C (%) | H (%) | N (%) |
|---|---|---|---|
| Calcd. | 76.47 | 8.78 | 9.39 |
| Found | 76.60 | 8.99 | 9.35 |

The following compound of Example 50 was obtained in the same manner as described in Example 49.

Example 50

4-Cyclohexyl-1-ethyl-5,7-dimethyl-1,8-naphthyridin-2(1H)-one

Starting compounds: 6-amino-4-cyclohexyl-1-ethyl-2(1H)-pyridone and 2,4-pentanedione Melting point 117°–118° C. (hexane)

Elemental analysis data (for $C_{18}H_{24}N_2O$)

|  | C (%) | H (%) | N (%) |
|---|---|---|---|
| Calcd. | 76.02 | 8.51 | 9.85 |
| Found | 76.12 | 8.65 | 9.81 |

Chemical structures of the compounds obtained in Examples 1 to 50 are shown in the following tables.

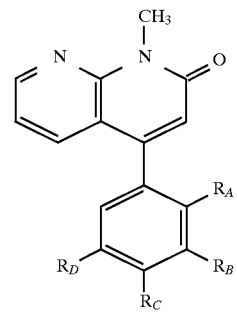

| Example No. | $R_A$ | $R_B$ | $R_C$ | $R_D$ |
|---|---|---|---|---|
| 1 | H | Cl | H | H |
| 2 | H | H | H | H |
| 3 | H | —CH$_3$ | H | H |
| 4 | —CH$_3$ | H | H | H |
| 5 | H | —OCH$_3$ | H | H |
| 6 | H | H | Cl | H |
| 7 | H | Br | H | H |
| 8 | Cl | Cl | H | H |
| 9 | H | Cl | H | Cl |
| 10 | H | —CF$_3$ | H | H |
| 36 | H | —OH | H | H |

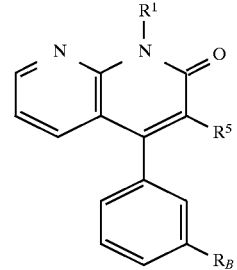

| Example No. | $R^1$ | $R^5$ | $R_B$ |
|---|---|---|---|
| 11 | —CH$_3$ | H | —CN |
| 12 | —CH$_3$ | H | —NO$_2$ |
| 13 | —CH$_3$ | —CH$_3$ | H |
| 14 | —CH$_2$CH$_3$ | H | H |
| 15 | —CH$_2$CH$_3$ | H | Cl |
| 16 | —CH$_2$CH$_2$CH$_3$ | H | H |
| 17 | —CH(CH$_3$)$_2$ | H | H |

-continued

| | | | |
|---|---|---|---|
| 18 | cyclopropyl | H | H |
| 19 | cyclobutyl | H | H |
| 20 | phenyl | H | H |
| 21 | —(CH₂)₄—phenyl | H | —NO₂ |
| 22 | —CH₂-pyridyl | H | H |
| 23 | —CH₃ | H | —NH₂ |
| 37 | —CH₂CH₃ | H | Br |
| 41 | —CH₂—C≡CH | H | H |
| 42 | —CH₂CN | H | H |

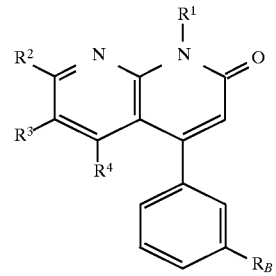

| Example No. | R¹ | R² | R³ | R⁴ | R_B |
|---|---|---|---|---|---|
| 24 | —CH₃ | —CH₃ | H | —CH₃ | Cl |
| 25 | —CH₃ | —CH₃ | —CH₃ | —CH₃ | H |
| 26 | —CH₃ | —CH₂CH₃ | H | —CH₃ | H |
| 27 | —CH₃ | —CH₂CH₃ | H | —CH₃ | Cl |
| 28 | —CH₃ | —CH₂CH₃ | H | —CH₂CH₃ | H |
| 29 | —CH₂CH₃ | —CH₃ | H | —CH₃ | Cl |
| 30 | —CH₂CH₃ | —CH₃ | H | —CH₃ | Br |

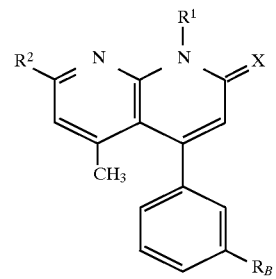

| Example No. | R¹ | R² | R_B | X |
|---|---|---|---|---|

-continued

| | | | | |
|---|---|---|---|---|
| 31 | —CH₂CH₃ | —CH₂CH₂ | Br | O |
| 32 | —CH₂CH₂CH₃ | —CH₃ | Br | O |
| 33 | —CH₂CH₂CH₃ | —CH₂CH₃ | Br | O |
| 34 | cyclopropyl | —CH₃ | Cl | O |
| 35 | cyclopropyl | —CH₂CH₃ | Cl | O |
| 38 | —CH₂CH₃ | —CH₃ | H | O |
| 39 | —CH₂CH₃ | —CH₂CH₃ | Cl | O |
| 40 | —CH₂CH₃ | —CH₂CH₃ | H | O |
| 43 | —CH₃ | —CH₂CH₃ | Cl | S |
| 44 | —CH₂CH₃ | —CH₃ | H | S |

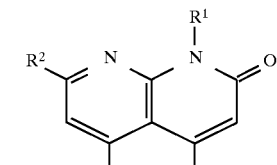

| Example No. | R¹ | R² | R⁴ | R⁶ | Salt |
|---|---|---|---|---|---|
| 45 | —CH₂CH₃ | H | H | cyclohexyl | — |
| 46 | —CH₂CH₃ | H | H | cyclohexyl | 0.45 HCl |
| 47 | —CH₂CH₃ | H | H | cyclopentyl | — |
| 48 | —CH₂CH₃ | H | H | adamantyl | — |
| 49 | —CH₂CH₃ | —CH₂CH₃ | —CH₃ | cyclohexyl | — |
| 50 | —CH₂CH₃ | —CH₃ | —CH₂ | cyclohexyl | — |

Compounds shown in the following tables were obtained making use of the similar methods of the aforementioned Examples 1 to 50 and the modified methods thereof known to those skilled in the art.

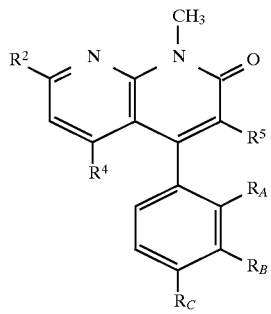

| Example No. | $R^2$ | $R^4$ | $R^5$ | $R_A$ | $R_B$ | $R_C$ | Melting point |
|---|---|---|---|---|---|---|---|
| 51 | H | H | H | H | H | —CH$_3$ | 135.5~136.0° C. (iPr$_2$O) |
| 52 | H | H | H | H | F | H | 144~145° C. (AcOEt-iPr$_2$O) |
| 53 | H | H | H | Cl | H | H | 136~137° C. (AcOEt-iPr$_2$O) |
| 54 | H | H | H | H | Cl | Cl | 186~188° C. (AcOEt) |
| 55 | H | H | —CH$_3$ | H | —OCH$_3$ | H | 84~85° C. (iPr$_2$O-hexane) |
| 56 | —CH$_2$CH$_3$ | —CH$_2$CH$_3$ | H | H | Cl | H | 76~77° C. (iPr$_2$O-hexane) |
| 57 | —CH$_2$CH$_2$CH$_3$ | —CH$_2$CH$_2$CH$_3$ | H | H | H | H | 61~62° C. (iPr$_2$O-hexane) |
| 58 | —(CH$_2$)$_3$—CH$_3$ | —CH$_3$ | H | H | H | H | 74~76° C. (hexane) |
| 59 | —CH(CH$_3$)$_2$ | —CH(CH$_3$)$_2$ | H | H | H | H | 82~83° C. (hexane) |
| 60 | —CH$_2$CH(CH$_3$)$_2$ | —CH$_3$ | H | H | H | H | 92~93° C. (hexane) |

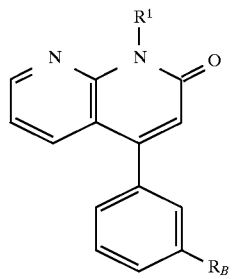

| Example No. | $R^1$ | $R_B$ | Melting point |
|---|---|---|---|
| 61 | —(CH$_2$)$_3$—CH$_3$ | H | 96.0~96.5° C. (iPr$_2$O) |
| 62 | cyclopentyl | H | 115.5~116.0° C. (iPr$_2$O) |
| 63 | cyclohexyl | H | 161~163° C. (iPr$_2$O) |

-continued

| | | | Melting point |
|---|---|---|---|
| 64 | —CH₂—(phenyl) | H | 154~155° C. (iPr₂O) |
| 65 | —(CH₂)₂—(phenyl) | H | 143.0~144.5° C. (iPr₂O) |
| 66 | —(CH₂)₃—(phenyl) | H | 92.0~92.5° C. (iPr₂O) |
| 67 | —(CH₂)₄—(phenyl) | H | 82.0~83.0° C. (iPr₂O) |
| 68 | —CH₂—(3-pyridyl) | H | 121.0~122.0° C. (iPr₂O) |
| 69 | —CH₂CH=CH₂ | H | 107~108° C. (iPr₂O) |
| 70 | —CH₂—(cyclopropyl) | H | 80~81° C. (iPr₂O-hexane) |
| 71 | —CH₂CH₃ | —CH₃ | 60~62° C. (iPr₂O-hexane) |
| 72 | —(CH₂)₂N(CH₃)₂ | H | 95~98° C. (iPr₂O) |
| 73 | —CH₂—(cyclopropyl) | Cl | 112.5~113° C. (iPr₂O-hexane) |
| 74 | —CH₂CH=CH₂ | Cl | 106~106.5° C. (iPr₂O) |
| 75 | —CH₂CO₂CH₂CH₃ | H | 87~88° C. (iPr₂O) |
| 76 | —CH₂CO₂H | H | 215~218° C. (AcOEt) |
| 77 | —CH₂COCH₃ | H | 161~164° C. (AcOEt-iPr₂O) |
| 78 | —CH₂CONH₂ | H | 185~188° C. (dioxane-H₂O) |
| 79 | —CH₂—(2-pyridyl) | Cl | 137~139° C. (AcOEt-iPr₂O) |
| 80 | —(CH₂)₂—(3-pyridyl) | Cl | 146~147° C. (AcOEt-iPr₂O) |

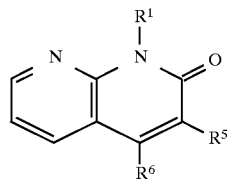

| Example No. | R¹ | R⁵ | R⁶ | Melting point |
|---|---|---|---|---|
| 81 | —CH₂CH₃ | H | (2-thienyl) | 116~117° C. (iPr₂O) |

-continued
| | | | | |
|---|---|---|---|---|
| 82 | —CH₂CH₃ | H |  | 137~139° C. (iPr₂O) |
| 83 | —CH₂CH₃ | H |  | 188~190° C. (AcOEt) |
| 84 | 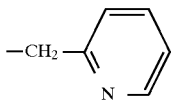 | H |  | 188~190° C. (AcOEt-iPr₂O) |
| 85 | —CH₂CH₃ | —CH₃ |  | 158~160° C. (iPr₂O-hexane) |
| 86 | —CH₃ | —CH₂CH₃ |  | 137~139° C. (iPr₂O) |
| 87 | —CH₃ | —CH₂CH₂CH₃ |  | 118~119° C. (iPr₂O) |
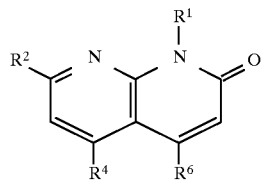
| Example No. | R¹ | R² | R⁴ | R⁶ | Melting point |
|---|---|---|---|---|---|
| 88 | —CH₃ | —CH₃ | 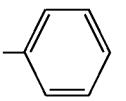 |  | 173~175° C. (AcOEt-iPr₂O) |
| 89 | —CH₃ | H | —CF₃ |  | 186~186.5° C. (AcOEt-iPr₂O) |
| 90 | —CH₂CH₃ | —CH₃ | H |  | 105~107° C. (iPr₂O-hexane) |
| 91 | —CH₂CH₃ | —CH₃ | H | 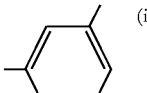 | 112~113° C. (iPr₂O-hexane) |
| 92 | —CH₂CH₃ | —CH₂CH₃ | H | 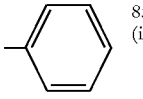 | 85~86° C. (iPr₂O-hexane) |
| 93 | —CH₂CH₃ | —CH₃ | H | 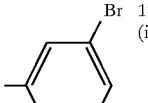 | 127~128° C. (iPr₂O-hexane) |

| 94 | —CH$_2$CH$_3$ | —CH$_2$CH$_3$ | H | 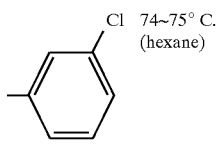 Cl | 74~75° C. (hexane) |

In addition to the aforementioned compounds of Examples, the following shows still further compounds of the present invention. These compounds can be synthesized making use of the aforementioned production methods, the synthetic pathways and methods described in Examples and the modified methods thereof known to those skilled in the art, without special experiments.

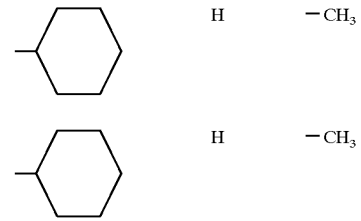

| Compound No. | R$^1$ | R$^2$ | R$^4$ | R$_B$ |
|---|---|---|---|---|
| A-1 | —CH$_2$CH$_3$ | —CH$_2$CH$_3$ | —CH$_3$ | —CH$_3$ |
| A-2 | —CH$_2$CH$_3$ | —CH$_2$CH$_3$ | —CH$_3$ | —CH$_2$CH$_3$ |
| A-3 | —CH$_2$CH$_3$ | —CH$_2$CH$_3$ | H | —CH$_3$ |
| A-4 | —CH$_2$CH$_3$ | —CH$_2$CH$_3$ | H | —CH$_2$CH$_3$ |
| A-5 | —CH$_2$CH$_3$ | —CH$_2$CH$_3$ | H | —OCH$_3$ |
| A-6 | —CH$_3$ | H | H | —SH |
| A-7 | —CH$_2$CH$_3$ | —CH$_2$CH$_3$ | H | —SCH$_3$ |
| A-8 | —CH$_2$CH$_3$ | —CH$_3$ | H | I |
| A-9 | —CH$_2$CH$_3$ | —CH$_2$CH$_3$ | H | Br |
| A-10 | —CH$_2$CH$_3$ | —CH$_2$CH$_3$ | H | I |
| A-11 | —CH$_2$CH$_3$ | —CH$_2$CH$_3$ | —CH$_3$ | I |
| A-12 | —CH$_3$ | H | H | —NHCH$_3$ |
| A-13 | —CH$_3$ | H | H | —N(CH$_3$)$_2$ |
| A-14 | —CH$_3$ | H | H | —NHCOCH$_3$ |
| A-15 | —CH$_3$ | H | H | —COOH |
| A-16 | —CH$_3$ | H | H | —COOCH$_3$ |
| A-17 | —CH$_3$ | H | H | —CONH$_2$ |
| A-18 | —CH$_3$ | H | H | —CONHCH$_3$ |
| A-19 | —CH$_3$ | H | H | —COCH$_3$ |

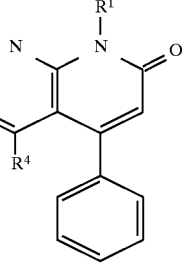

| Compound No. | R$^1$ | R$^2$ | R$^3$ | R$^4$ |
|---|---|---|---|---|
| A-20 | —CH$_3$ | —OH | H | H |
| A-21 | —CH$_2$CH$_3$ | —OH | H | H |
| A-22 | —CH$_3$ | Cl | H | H |
| A-23 | —CH$_2$CH$_3$ | Cl | H | H |
| A-24 | —CH$_3$ | —OCH$_3$ | H | H |
| A-25 | —CH$_3$ | —NH$_2$ | H | H |
| A-26 | —CH$_3$ | —N(CH$_3$)$_2$ | H | H |
| A-27 | —CH$_3$ | —CH$_3$ | —NO$_2$ | —CH$_3$ |
| A-28 | —CH$_3$ | —CH$_3$ | —NHCOCH$_3$ | —CH$_3$ |
| A-29 | —CH$_3$ | —CH$_3$ | —CN | —CH$_3$ |
| A-30 | —CH$_3$ | —CH$_3$ | —COOH | —CH$_3$ |
| A-31 | —CH$_3$ | —CH$_3$ | —COOCH$_3$ | —CH$_3$ |
| A-32 | —CH$_3$ | —CH$_3$ | —CHO | —CH$_3$ |
| A-33 | —CH$_3$ | —CH$_3$ | —CONH$_2$ | —CH$_3$ |
| A-34 | —CH$_3$ | —CH$_3$ | —CONHCH$_3$ | —CH$_3$ |
| A-35 | —CH$_3$ | cyclohexyl | H | —CH$_3$ |
| A-36 | —CH$_2$CH$_3$ | cyclohexyl | H | —CH$_3$ |
| A-37 | —CH$_3$ | H | H | —NO$_2$ |
| A-38 | —CH$_2$CH$_3$ | H | H | —NO$_2$ |

| Compound No. | R$^1$ | R$^4$ |
|---|---|---|
| A-39 | —CH$_3$ | —OH |
| A-40 | —CH$_3$ | —SH |
| A-41 | —CH$_2$CH$_3$ | Cl |
| A-42 | —CH$_3$ | —SH |
| A-43 | —CH$_2$CH$_3$ | —SCH$_3$ |
| A-44 | —CH$_3$ | —NH$_2$ |
| A-45 | —CH$_3$ | —NHCH$_3$ |
| A-46 | —CH$_3$ | —N(CH$_3$)$_2$ |
| A-47 | —CH$_3$ | —NHCOCH$_3$ |
| A-48 | —CH$_2$CH$_3$ | —CN |
| A-49 | —CH$_3$ | —COOH |
| A-50 | —CH$_3$ | —COOCH$_3$ |
| A-51 | —CH$_2$CH$_3$ | —CHO |
| A-52 | —CH$_3$ | —CONH$_2$ |
| A-53 | —CH$_3$ | —CONHCH$_2$ |

-continued

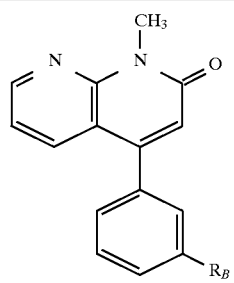

| Compound No. | $R_B$ |
|---|---|
| A-54 | $-NHCH_3$ |
| A-55 | $-N(CH_3)_2$ |
| A-56 | $-NHCOCH_3$ |
| A-57 | $-COOH$ |
| A-58 | $-COOCH_3$ |
| A-59 | $-CONH_2$ |
| A-60 | $-CONHCH_3$ |
| A-61 | $-CON(CH_3)_2$ |
| A-62 | I |
| A-63 | $-COCH_3$ |
| A-64 | $-CH_2CH_3$ |

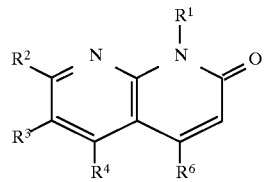

| Compound No. | $R^1$ | $R^6$ | Compound No. | $R^1$ | $R^6$ |
|---|---|---|---|---|---|
| B-1 | $-CH_3$ | cyclopentyl | B-6 | $-C_3H_7$ | cyclohexyl |
| B-2 | $-CH_3$ | cyclohexyl | B-7 | $-C_3H_7$ | cycloheptyl |
| B-3 | $-CH_3$ | cycloheptyl | B-8 | $-CH_3$ | adamantyl |
| B-4 | $-C_2H_5$ | cycloheptyl | B-9 | $-C_3H_7$ | adamantyl |
| B-5 | $-C_3H_7$ | cyclopentyl | | | |

-continued

| Compound No. | $R^1$ | $R^2$ | $R^3$ | $R^4$ | $R^6$ |
|---|---|---|---|---|---|
| B-10 | $-C_2H_5$ | $-CH_3$ | H | $-CH_3$ | cyclohexyl |
| B-11 | $-C_2H_5$ | $-C_2H_5$ | H | $-C_2H_5$ | cyclohexyl |
| B-12 | $-C_2H_5$ | $-CH_3$ | $-CH_3$ | $-CH_3$ | cyclohexyl |
| B-13 | $-C_2H_5$ | cyclohexyl | H | $-CH_3$ | cyclohexyl |
| B-14 | $-C_3H_7$ | $-CH_3$ | H | $-CH_3$ | cyclohexyl |
| B-15 | $-C_3H_7$ | $-C_2H_5$ | H | $-CH_3$ | cyclohexyl |
| B-16 | $-C_3H_7$ | $-C_2H_5$ | H | $-C_2H_5$ | cyclohexyl |
| B-17 | $-C_3H_7$ | $-CH_3$ | $-CH_3$ | $-CH_3$ | cyclohexyl |
| B-18 | $-C_2H_5$ | $-CH_3$ | H | $-CH_3$ | cyclopentyl |
| B-19 | $-C_2H_5$ | $-C_2H_5$ | H | $-CH_3$ | cyclopentyl |
| B-20 | $-C_2H_5$ | $-CH_3$ | H | $-CH_3$ | cycloheptyl |

| | | | | |
|---|---|---|---|---|
| B-21 | —C₂H₅ | —C₂H₅ | H | —CH₃ 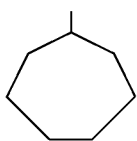 |

We claim:

1. A 1,8-naphthyridine derivative represented by the following Formula (I), a salt thereof, a hydrate thereof or a solvate thereof

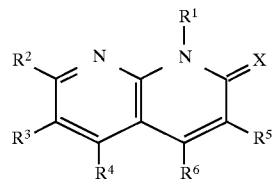

each symbol in the formula represents the following meaning:

X: an oxygen atom or a sulfur atom, $R^1$ is a lower alkyl group which may be substituted with a group described in the A group, a lower alkenyl group, a lower alkynyl group, a cycloalkyl group, a cycloalkyl-lower alkyl group, an aryl group which may be substituted with a group described in the B group, an aralkyl group which may be substituted with a group described in the B group, a five- or six-membered monocyclic heteroaryl group, or a five- or six membered monocyclic heteroaryl-lower alkyl group, $R^2$ is a hydrogen atom, a halogen atom, a lower alkyl group, a hydroxy group, a lower alkoxy group, a lower alkylcarbonyl group, a trihalogenomethyl group, a nitro group, a cyano group, an amino group, a mono- or di-lower alkylamino group, a carboxyl group, a lower alkoxycarbonyl group, a carbamoyl group, a mono- or di-lower alkylcarbamoyl group, a lower alkylcarbonylamino group, an aryl group or a cycloalkyl group, $R^3$ and $R^4$: may be the same or different from each other and each represents a hydrogen atom, a halogen atom, a lower alkyl group, a hydroxyl group, a lower alkoxy group, a lower alkylcarbonyl group, a trihalogenomethyl group, a nitro group, a mono- or di-lower alkylamino group, a carboxyl group, a lower alkoxycarbonyl group, a carbamoyl group, a mono- or di-lower alkylcarbamoyl group, a lower alkylcarbonylamino group, an aryl group or a cycloalkyl group, $R^5$: a hydrogen atom, $R^6$: an aryl group which may be substituted with a group described in the C group, a five- or six-membered monocyclic heteroaryl group which may be substituted with a group described in the C group, a cycloalkyl group or an adamantyl group;

the A group is halogen atom, a hydroxyl group, a lower alkoxy group, a cyano group, a nitro group, an amino group, a mono- or di-lower alkylamino group, a carboxyl group, a lower alkoxycarbonyl group, a lower alkylcarbonyl group, a carbamoyl group or a mono- or di-lower alkylcarbamoyl group;

The B group is a lower alkyl group or a group described in the A group;

The C group is a halogen atom, a hydroxyl group, a lower alkoxy group, a lower alkylcarbonyl group, a nitro group, a cyano group, an amino group, a mono- or di-lower alkylamino group, a carboxyl group, a lower alkoxycarbonyl group, a carbamoyl group, a mono- or di-lower alkylcarbamoyl group or a lower alkylcarbonylamino group, or a lower alkyl group which may be substituted with these groups, with the proviso that, when each of $R^1$, $R^2$ and $R^4$ is a methyl group and each of $R^3$ and $R^5$ is a hydrogen atom, $R^6$ represents an aryl group which is substituted with a group described in the C group, a five- or six-membered monocylic heteroaryl group which may be substituted with a group described in the C group, a cycloalkyl group, or an adamantyl group.

2. The 1,8-naphthyridine derivative or a salt thereof according to claim 1, wherein $R^1$ is a lower alkyl group which may be substituted with a group described in the A group, a lower alkenyl group, a lower alkynyl group, a cycloalkyl group, a cycloalkyl-lower alkyl group, a phenyl group, a phenyl-lower alkyl group, a pyridyl group or a pyridyl-lower alkyl group, and $R^2$, $R^3$ and $R^4$ may be the same or different from one another and each represents a hydrogen atom, a halogen atom, a lower alkyl group, a hydroxyl group, a lower alkoxy group, a lower alkylcarbonyl group, a trihalogenomethyl group, a phenyl group or a cycloalkyl group, and $R^6$ is a phenyl group which may be substituted with a group described in the C group, a thienyl group, a thiazolyl group, a cycloalkyl group or an adamantyl group, and C group is a halogen atom, a hydroxyl group, a lower alkoxy group, a lower alkylcarbonyl group, a nitro group, a cyano group, an amino group, a mono- or di-lower alkylamino group, a carboxyl group, a lower alkoxycarbonyl group, a carbamoyl group, a mono- or di-lower alkylcarbamoyl group or a lower alkylcarbonylamino group, or a lower alkyl group which may be substituted with a halogen atom or hydroxyl group.

3. The 1,8-naphthyridine derivative or a salt thereof according to claim 2, wherein $R^1$ is a lower alkyl group which may be substituted with a group selected from a cyano group, a mono- or di-lower alkylamino group, a carboxyl group, a lower alkoxycarbonyl group, a lower alkylcarbonyl group or a carbamoyl group, a lower alkenyl group, a lower alkynyl group, a cycloalkyl group, a cycloalkyl-lower alkyl group, a phenyl group, a phenyl-lower alkyl group, a pyridyl group or a pyridyl-lower alkyl group, and $R^6$ is a phenyl group which may be substituted with a group selected from a halogen atom, a hydroxyl group, a lower alkyl group, a lower alkoxy group, a nitro group, a cyano group, an amino group or a trifluoromethyl group, thienyl group, thiazolyl group, a cycloalkyl group or an adamantyl group, and $R^2$, $R^3$ and $R^4$ may be the same or different from one another and each represents a hydrogen atom, a lower alkyl group, a trifluoromethyl group or a phenyl group.

4. The 1,8-naphthyridine derivative or a salt thereof according to claim 1, wherein $R^6$ is a phenyl group which may be substituted with a halogen atom, a hydroxyl group, a lower alkyl group, a lower alkoxy group, a nitro group, a cyano group or an amino group.

5. The 1,8-naphthyridine derivative or a salt thereof according to claim 1, wherein $R^6$ is a cycloalkyl group or an adamantyl group.

6. The 1,8-naphthyridine derivative or a salt thereof according to claim 1, wherein X is an oxygen atom.

7. A naphthyridine derivative selected from the group consisting of 4-(3-chlorophenyl)-7-ethyl-1,5-dimethyl-1,8-naphthyridin-2(1H)-one or a salt thereof, 4-(3-bromophenyl)-1-ethyl-5,7-dimethyl-1,8-naphthyridin-2-(1H)-one or a salt thereof, 4-(3-bromophenyl)-1,7-diethyl-5-methyl-1,8-naphthyridin-2(1H)-one or a salt thereof, 1,7-diethyl-5-methyl-4-phenyl-1,8-naphthyridin-2(1H)-one or a salt thereof, 4-cyclohexyl-1-ethyl-1,8-naphthyridin-2(1H)-one or a salt thereof and 4-(3-bromophenyl)-1-ethyl-7-methyl-1,8-naphthyridin-2-(1H)-one or a salt thereof.

8. The naphthyridine derivative of claim 7 which is 4-(3-Chlorophenyl)-7-ethyl-1,5-dimethyl-1,8-naphthyridin-2(1H)-one or a salt thereof.

9. The naphthyridine derivative of claim 7 which is 4-(3-bromophenyl)-1-ethyl-5,7-dimethyl-1,8-naphthyridin-2(1H)-one or a salt thereof.

10. The naphthyridine derivative of claim 7 which is 4-(3-bromophenyl)-1,7-diethyl-5-methyl-1,8-naphthyridin-2(1H)-one or a salt thereof.

11. The naphthyridine derivative of claim 7 which is 1,7-diethyl-5-methyl-4-phenyl-1,8-naphthyridin-2(1H)-one or a salt thereof.

12. The naphthyridine derivative of claim 7 which is 4-cyclohexyl-1-ethyl-1,8-naphthyridin-2(1H)-one or a salt thereof.

13. The naphthyridine derivative of claim 7 which is 4-(3-bromophenyl)-1-ethyl-7-methyl-1,8-naphthyridine-2(1H)-one or a salt thereof.

14. A pharmaceutical composition which comprises the 1,8-naphthyridine derivative as claimed in claim 1 and a pharmaceutically acceptable carrier or diluent.

15. The pharmaceutical composition according to claim 14, which is a type IV phosphodiesterase inhibitor.

16. The pharmaceutical composition according to claim 15, which is a type IV phosphodiesterase inhibitor that is a preventive or therapeutic agent for respiratory diseases comprising bronchial asthma, chronic bronchitis, pneumonia and adult respiratory distress syndrome (ARDS).

17. The pharmaceutical composition according to claim 15, which is a type IV phosphodiesterase inhibitor that is a preventive or therapeutic agent for inflammatory diseases comprising atopic dermatitis, conjunctivitis, urticaria, acquired immunodeficiency syndrome (AIDS), keloid formation, rhinitis, iridocyclitis, gingivitis, periodontitis, alveolar pyorrhea, gastritis, ulcerative colitis, Crohn disease, gastrointestinal ulcer, esophagitis, myositis, encephalitis (myasthenia gravis, multiple sclerosis and neuritis), hepatitis, cicatrization, nephritis including proliferative nephritis, peritonitis, pleurisy, scleroderma and burn injury.

18. The pharmaceutical composition according to claim 16 wherein said bronchial asthma is atopic asthma.

19. A method for inhibiting the activity of type IV phosphodiesterase in a patient which comprises administering to said patient a type IV phosphodiesterase inhibiting amount of the pharmaceutical composition of claim 14.

20. A method for treating a respiratory disease in a patient which comprises administering to said patient a therapeutically effective amount of the pharmaceutical composition of claim 14.

* * * * *

UNITED STATES PATENT AND TRADEMARK OFFICE
CERTIFICATE OF CORRECTION

PATENT NO. : 5,817,670
DATED : October 6, 1998
INVENTOR(S) : Kazuhisa Takayama, Masahiro Iwata, Yoshinori Okamoto, Motonori Aoki, Akira Niwa and Yasuo Isomura It is certified that error appears in the above-indentified patent and that said Letters Patent is hereby corrected as shown below:

At Column 20, line 5 should read:

"Compound Type IV   Type I   Type II   Type III   Type V"

Signed and Sealed this

Second Day of February, 1999

Attest:

Attesting Officer

*Acting Commissioner of Patents and Trademarks*